US012805465B2

(12) United States Patent
Nguyen et al.

(10) Patent No.: US 12,805,465 B2
(45) Date of Patent: Nov. 24, 2026

(54) ***Brassica napus* PLANTS COMPRISING AN IMPROVED FERTILITY RESTORER**

(71) Applicant: BASF AGRICULTURAL SOLUTIONS US LLC, Florham Park, NJ (US)

(72) Inventors: Thi Ninh Thuan Nguyen, Deinze (BE); Remy Adriaensen, Deinze (BE); Geoffrey Wagner, Ghent (BE); Antje Rohde, Ghent (BE); Natasa Formanova, Engelberg (CH)

(73) Assignee: BASF AGRICULTURAL SOLUTIONS US LLC, Research Triangle Park, NC (US)

( * ) Notice: Subject to any disclaimer, the term of this patent is extended or adjusted under 35 U.S.C. 154(b) by 424 days.

(21) Appl. No.: 18/268,660

(22) PCT Filed: Dec. 20, 2021

(86) PCT No.: PCT/US2021/073033

§ 371 (c)(1),
(2) Date: Jun. 21, 2023

(87) PCT Pub. No.: WO2022/140762

PCT Pub. Date: Jun. 30, 2022

(65) Prior Publication Data

US 2024/0292798 A1 Sep. 5, 2024

(30) Foreign Application Priority Data

Dec. 21, 2020 (EP) .................................... 20215999

(51) Int. Cl.
*A01H 6/20* (2018.01)
*A01H 1/00* (2006.01)
*A01H 1/04* (2006.01)

(52) U.S. Cl.
CPC ............ *A01H 6/202* (2018.05); *A01H 1/045* (2021.01); *A01H 1/123* (2021.01)

(58) Field of Classification Search
None
See application file for complete search history.

(56) References Cited

U.S. PATENT DOCUMENTS 5,545,821 A 8/1996 Wong et al.

FOREIGN PATENT DOCUMENTS

EP 0242236 A1 10/1987
EP 0242246 A1 10/1987
EP 0507698 A1 10/1992
EP 0508909 A1 10/1992
(Continued)

OTHER PUBLICATIONS

Of Lubos-Sujo 2018 (Dissertation: "Characterization and improvement of Ogu-INRA CMS *Brassica napus* L. fertility restorers." (Year : 2018).*
(Continued)

*Primary Examiner* — Matthew R Keogh
(74) *Attorney, Agent, or Firm* — ArentFox Schiff LLP

(57) ABSTRACT

The invention provides fertility restorer *Brassica napus* plants, plant material and seeds, characterized in that these products harbor a specific introgression fragment of the Ogura fertility restorer at the end of chromosome N10. Tools are also provided which allow detection of the fertility restorer.

21 Claims, 5 Drawing Sheets

Specification includes a Sequence Listing.

(56) References Cited

FOREIGN PATENT DOCUMENTS

| | | | |
|---|---|---|---|
| EP | 0534858 | A1 | 3/1993 |
| EP | 1493328 | A1 | 1/2005 |
| WO | 98/27806 | A1 | 7/1998 |
| WO | 98/56948 | A1 | 12/1998 |
| WO | 01/41558 | A1 | 6/2001 |
| WO | 02/36831 | A2 | 5/2002 |
| WO | 2005/002324 | A2 | 1/2005 |
| WO | 2005/074671 | A1 | 8/2005 |
| WO | 2009/007091 | A2 | 1/2009 |
| WO | 2009/068313 | A2 | 6/2009 |
| WO | 2009/100178 | A2 | 8/2009 |
| WO | 2010/006732 | A2 | 1/2010 |
| WO | 2011/020698 | A1 | 2/2011 |
| WO | 2011/060946 | A1 | 5/2011 |
| WO | 2011/153186 | A1 | 12/2011 |
| WO | 2012/071040 | A1 | 5/2012 |
| WO | 2017/025420 | A1 | 2/2017 |

OTHER PUBLICATIONS

Asselin 2012 (Thesis: "Seed Quality Imporvement in the ogu-INRA CMS System in Oilseed Rape (*Brassica napus* L.)") (Year: 2012).*
Wu et al.2020 (Plant Biotechnology Journal 18: p. 1857-1859) (Year: 2020).*
Udall et al.2005 (Genetics 169:2 p. 967-979) (Year: 2005).*
Wu Z. Dec. 2020 (Dissertation: "Mechanism and Utilization of Alloplasmic Male-Sterile Lines in *Brassica juncea*." Huazhong Agricultural University; Wuhan, China) (Year: 2020).*
Schraz et al 2006 (Trends in Plant Science 11:11 p. 536-542) (Year: 2006).*
Delourme et al 2013 (BMC Genomics 14:120 p. 1-18) (Year: 2013).*
Allen, et al., "Transcript-specific, single-nucleotide polymorphism discovery and linkage analysis in hexaploid bread wheat (*Triticum aestivum* L.)", Plant biotechnology journal, vol. 9, Issue 9, Jun. 1, 2011, pp. 1086-1099.
Barret, et al., "Development of a SCAR (sequence characterised amplified region) marker for molecular tagging of the dwarf Breizh (Bzh) gene in *Brassica napus* L", Theoretical and Applied Genetics, vol. 97, Oct. 1998, pp. 828-833.
Bayer, et al., "Assembly and comparison of two closely related Brassica napus genomes", Plant Biotechnology Journal, vol. 15, Issue 12, Apr. 12, 2017, pp. 1602-1610.
Bortesi, et al., "Patterns of CRISPR/Cas9 activity in plants, animals and microbes", Plant biotechnology journal, vol. 14, Issue 12, Sep. 10, 2016, pp. 2203-2216.
Botstein, et al., "Construction of a genetic linkage map in man using restriction fragment length polymorphisms", American journal of human genetics, vol. 32, Issue 3, May 1980, pp. 314-331.
Burstein, et al., "New CRISPR-Cas systems from uncultivated microbes", Nature, vol. 542, Dec. 22, 2016, pp. 237-241.
Delourme, et al., "Radish cytoplasmic male sterility in rapeseed: Breeding restorer lines with a good female fertility", Breeding: Methodology, GCIRC 1991 Congress, 1991, pp. 1506-1510.
Diethard Tautz, "Hypervariability of simple sequences as a general source for polymorphic DNA markers", Nucleic acids research, vol. 17, Issue 16, Aug. 25, 1989, pp. 6463-6471.
Dussle, et al., "Conversion of AFLP fragments tightly linked to SCMV resistance genes Scmv1 and Scmv2 into simple PCR-based markers", Theoretical and Applied Genetics, vol. 105, Dec. 2002, pp. 1190-1195.
Grey, et al., "Herbicide-resistant canola (*Brassica napus*) response and weed control with postemergence herbicides", Weed technology, vol. 20, Issue 3, Sep. 2006, pp. 551-557.
Gudi, et al., "Physical mapping of introgressed chromosome fragment carrying the fertility restoring (Rfo) gene for Ogura CMS in *Brassica juncea* L. Czern & Coss", Theoretical and Applied Genetics, vol. 133, Jul. 13, 2020, pp. 2949-2959.
Guo, et al., "AFLP and STS tagging of a major QTL for Fusarium head blight resistance in wheat", Theoretical and applied genetics, vol. 106, Apr. 2003, pp. 1011-1017.
Hu, et al., "Genetic diversity of 38 spinach (*Spinacia oleracea* L.) germplasm accessions and 10 commercial hybrids assessed by TRAP markers", Genetic resources and crop evolution, vol. 54, Feb. 16, 2007, pp. 1667-1674.
International Search Report for PCT Patent Application No. PCT/US2021/073033, Issued on May 30, 2022, 5 pages.
Komor, et al., "Programmable editing of a target base in genomic DNA without double-stranded DNA cleavage", Nature, vol. 533, Apr. 20, 2016, pp. 420-424.
Ma, et al., "CRISPR/Cas9 platforms for genome editing in plants: developments and applications", Molecular Plant, vol. 9, Issue 7, Jul. 2016, pp. 961-974.
Meksem, et al., "Conversion of AFLP bands into high-throughput DNA markers", Molecular Genetics and Genomics, vol. 265, Apr. 1, 2001, pp. 207-214.
Murovec, et al., "New variants of CRISPR RNA-guided genome editing enzymes", Plant biotechnology journal , vol. 15, Issue 8, Apr. 1, 2017, pp. 917-926.
Nakade, et al., "Cas9, Cpf1 and C2c1/2/3—What's next?", Bioengineered, vol. 8, Issue 3, 2017, pp. 265-273.
Negi, et al., "Identification of AFLP fragments linked to seed coat colour in *Brassica juncea* and conversion to a SCAR marker for rapid selection", Theoretical and Applied Genetics, vol. 101, Jul. 2000, pp. 146-152.
Osakabe, et al., "Genome editing with engineered nucleases in plants", Plant and Cell Physiology, vol. 56, Issue 3, Nov. 20, 2014, pp. 389-400.
Primard-Brisset, et al., "A new recombined double low restorer line for the Ogu-INRA cms in rapeseed (Brassica napus L.)", Theoretical and Applied Genetics, vol. 111, Issue 4, Jun. 18, 2005, pp. 736-746.
Tan, et al., "Imidazolinone-tolerant crops: history, current status and future", Pest Management Science: Formerly Pesticide Science, vol. 61, Issue 3, Dec. 31, 2004, pp. 246-257.
Tanksley, et al., "RFLP mapping in plant breeding: new tools for an old science", Nature biotechnology, vol. 7, Issue 3, Mar. 1, 1989, pp. 257-264.
Tian, et al., "Molecular marker-assisted breeding for improved Ogura cms restorer line (RfoRfo) and mapping of the restorer gene (Rfo) in *Brassica juncea*", Molecular Breeding, vol. 34, Jun. 6, 2014, pp. 1361-1371.
Vos, et al., "AFLP: a new technique for DNA fingerprinting", Nucleic acids research, vol. 23, Issue 21, Jan. 1, 1995, pp. 4407-4414.
Wang, et al., "Genetic characterization of a new radish introgression line carrying the restorer gene for Ogura CMS in Brassica napus", PloS one, vol. 15, Issue 7, Jul. 28, 2020, 14 pages.
Williams, et al., "DNA polymorphisms amplified by arbitrary primers are useful as genetic markers", Nucleic acids research, vol. 18, Issue 22, Nov. 25, 1990, pp. 6531-6535.
Xiaohui, et al., "A de novo genome of a Chinese radish cultivar", Horticultural Plant Journal, vol. 1, Issue 3, Nov. 2015, pp. 155-164.
Xu, et al., "Development of sequence-characterized amplified regions (SCARs) from amplified fragment length polymorphism (AFLP) markers tightly linked to the Vf gene in apple", Genome, vol. 44, Issue 1, Feb. 2001, pp. 63-70.

* cited by examiner

*Brassica napus* PLANTS COMPRISING AN IMPROVED FERTILITY RESTORER

CROSS-REFERENCE TO RELATED APPLICATIONS

This application is a National Stage Entry of PCT/US2021/073033, filed Dec. 20, 2021, which claims priority to European Patent Application No. 20215999.2, filed Dec. 21, 2020, the disclosures of each of which are hereby incorporated by reference in their entirety.

FIELD OF THE INVENTION

The invention relates to the field of fertility restoration in *Brassica napus*. Provided are *Brassica napus* plants comprising an Ogura restorer of fertility on chromosome N10. Also provided are methods and means to produce such plants, to produce hybrid seeds, and to detect the presence of the fertility restorer.

BACKGROUND OF THE INVENTION

*Brassica napus* is cultivated as one of the most valuable oil crops. As *Brassica napus* is typically 60-70% self pollinated, hybrid breeding in *Brassica* employs the use of systems based on male sterility. One type of cytoplasmic male sterility (CMS) which is used for hybrid breeding and hybrid production in *Brassica* is the Ogura (OGU) cytoplasmic male sterility. The Ogura male sterility can be restored by the fertility restorer for Ogura cytoplasmic male sterility. The Ogura fertility restorer has been transferred from *Raphanus sativus* (radish) into *Brassica.*

Initially, a large segment of the *Raphanus* genome was introgressed into *Brassica*. Not only has the introgression replaced part of the *Brassica napus* genome, it also resulted in high levels of glucosinolates and lower seed set. Abel et al (WO2017/025420) even determined that one arm of chromosome C09 was replaced by one arm of a *Raphanus* chromosome when the Ogura-introgression was created. Development of new recombinants and shortening the *Raphanus* fragment was hampered by the very low recombination rate in the region. Charne et al (WO98/27806) were able to remove part of the *Raphanus* fragment of the original restorer R40 and produced restorer lines with low glucosinolate levels. After that, several new recombination events have been described with reduced glucosinolate levels and better pod size (WO98/56948, WO2005/002324 ("R2000"), WO2005/074671 ("BLR-038"), WO2009/100178 ("SRF"), WO2011/020698 ("R7631").

Reduction of the size of the *Raphanus* fragment has however also led to loss of certain beneficial agronomic characteristics, such as podshatter tolerance (WO2017/025420). Abel et al have identified a shortened *Raphanus* fragment while maintaining the improved podshatter tolerance (WO2017/025420).

There remains a need for developing a restorer with a short introgression fragment, not associated with a deletion of *napus* genome while having good podshatter tolerance properties.

Summary of the Preferred Embodiments of the Invention

In a first embodiment of the invention, a *Brassica napus* plant comprising an Ogura restorer on chromosome N10. In a further aspect, the Ogura restorer of said *Brassica* plant is present at the end of chromosome N10. In yet another aspect, said Ogura restorer is present downstream of nucleotide 19,218,577 of chromosome N10, whereas in another aspect, said Ogura restorer is characterized by the presence of markers M2, M3 and M5, and by the absence of markers M1 and M4. In another embodiment, said Ogura restorer is characterized by the presence of a *Raphanus* chromosome fragment between position 8,330,119 and 10,655,049 of the *Raphanus* chromosome or a part thereof. In yet another embodiment, the *Brassica* plant according to the invention is a *Brassica napus* WOSR plant or a *Brassica napus* SOSR plant. In a further embodiment, said the Ogura restorer of said *Brassica* plant is obtainable from reference seeds deposited at NCIMB under accession number NCIMB 43628. In another embodiment the *Brassica* plant according to the invention restores the fertility of a CMS-Ogura *Brassica napus* plant. In a further embodiment, the Ogura restorer is present in homozygous form, whereas in another embodiment the *Brassica* plant according to the invention Ogura restorer in homozygous form is an inbred plant. In yet a further embodiment, the Ogura restorer is present in heterozygous form, whereas in another embodiment the *Brassica* plant according to the invention Ogura restorer in heterozygous form is a hybrid plant, said hybrid plant optionally further containing CMS-Ogura. Also provided is a part, seed or progeny of the *Brassica* plant according to the invention. Also provided is hybrid seed comprising the Ogura restorer according to the invention.

In yet another embodiment, the *Brassica* plant, part seed or progeny thereof or the hybrid seed according to the invention further comprise a technically induced mutant, such as an EMS induced mutant, or a modification in the genome created with genome editing technologies, a cisgene or a transgene. In another aspect, said technically induced mutant confers herbicide tolerance, such as tolerance to imidazolinone, or said transgene is a gene conferring herbicide tolerance, such as a gene which confers resistance to glufosinate or to glufosinate ammonium or a gene conferring resistance to glyphosate.

Also provided herein is a method for identifying a *Brassica napus* plant comprising the Ogura restorer according to the invention, said method comprising determining the presence of a *Raphanus* marker for Rfo-N10 in the genomic DNA of said plant. In another aspect, said marker is a marker in the region comprising nucleotide 8,600,416 to 9,251,274 of *Raphanus* chromosome R09, whereas in another aspect said marker is marker M2, M3 or M5.

In another embodiment, a method according to the invention for identifying a *Brassica napus* plant comprising the Ogura restorer is provided, said method further comprising determining the absence of a *Raphanus* marker absent in Rfo-N10 in the genomic DNA of said plant. In another aspect, said marker absent in Rfo-N10 is a marker in the region upstream of and including position 8,330,119 of *Raphanus* chromosome R09, or is a marker in the region downstream of and including position 10,655,049 excluding position 15,447,221-15,450,692, whereas in yet another aspect, said marker absent in Rfo-N10 is marker M1 or M4.

Also provided is a method for selecting a *Brassica napus* plant comprising the Ogura restorer according to the invention said method comprising identifying the presence of a *Raphanus* marker for Rfo-N10 according to the invention, and selecting a *Brassica napus* plant comprising said *Raphanus* marker for Rfo-N10.

It is another object of the invention to provide a method for producing a *Brassica napus* plant comprising the Ogura restorer according to the invention, said method comprising crossing a first *Brassica napus* plant comprising the Ogura restorer according to the invention with a second *Brassica napus* plant; and identifying, and optionally selecting, a progeny plant comprising Rfo-N10 according to the invention.

Also provided is method for producing hybrid *Brassica napus* seed, said method comprising providing a male *Brassica napus* plant comprising the Ogura restorer according to the invention, wherein said Ogura restorer is present in homozygous form; providing a female *Brassica napus* plant comprising CMS-Ogura; crossing said female *Brassica napus* plant with said male *Brassica napus* plant; and optionally harvesting seeds. A hybrid seed produced with said method is also provided herein, as well as a hybrid *Brassica napus* plant produced from said seed.

A further embodiment provides the use of the plant according to the invention for producing hybrid seed, and the use of the plant according to the invention for breeding.

Also provided herein is a method for the protection of a group of cultivated plants comprising technically induced mutant confers herbicide tolerance, such as tolerance to imidazolinone, or a transgene conferring herbicide tolerance, such as a gene which confers resistance to glufosinate or to glufosinate ammonium or a gene conferring resistance to glyphosate, according to the invention, in a field wherein weeds are controlled by the application of a composition comprising one or more herbicidal active ingredients, such as an imidazolinone herbicide, such as imazamox, or glufosinate or glufosinate ammonium or glyphosate.

DETAILED DESCRIPTION

Figure 1:
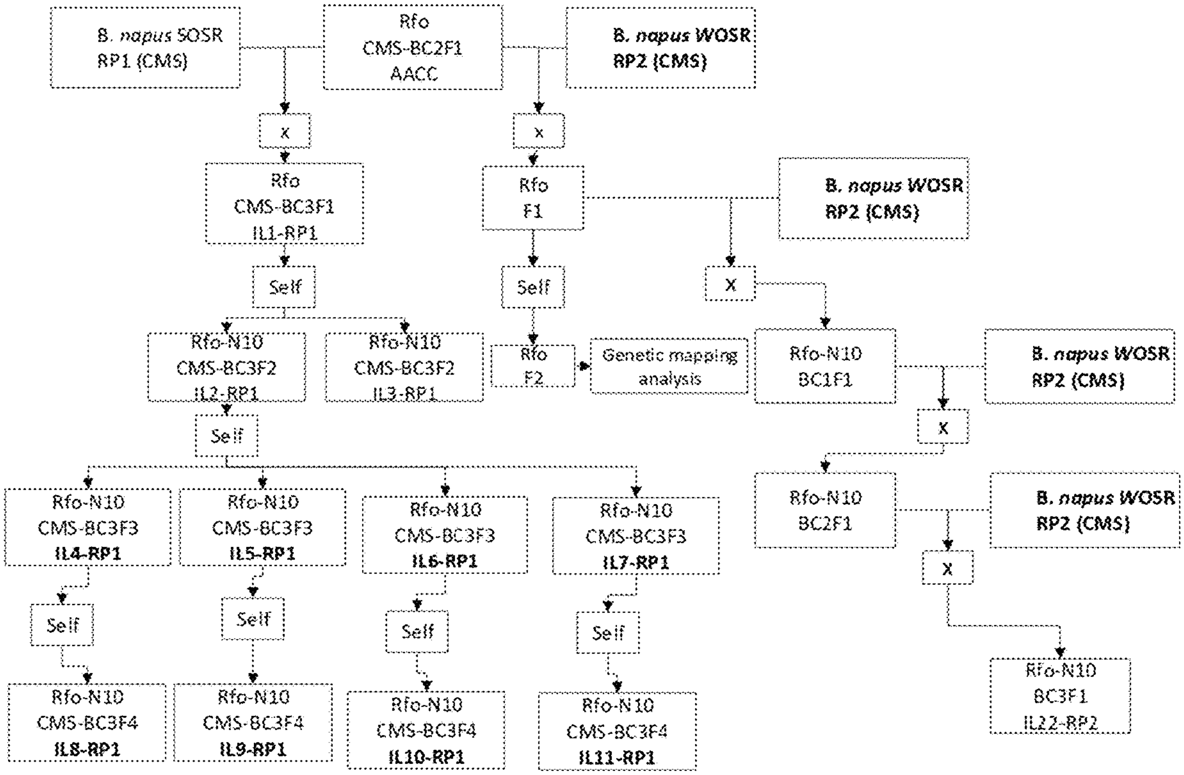
FIG. 1. Crossing and introgression schemes of Rfo-N10 in spring oilseed rape (SOSR) and winter oilseed rape (WOSR).

The current invention is based on the identification of a *Brassica napus* plant with a short Ogura restorer fragment at the end of chromosome N10.

In a first embodiment of the invention, a *Brassica napus* plant comprising an Ogura restorer on chromosome N10.

A "Ogura restorer" as used herein refers to a DNA sequence which is originating from *Raphanus sativus* (Radish) which restores Ogura cytoplasmic male sterility (CMS-Ogura), said CMS-Ogura having been transferred from radish as described by Pellan-Delourme et al (1987) Proc. 7th Int. Rapeseed Conf. Poznan, Poland, 199-203.

"Rfo-N10" as used herein refers to the Ogura restorer which is present on chromosome N10 of *Brassica napus.*

A "*Brassica napus* plant" or "*B. napus* plant" refers to allotetraploid or amphidiploid *Brassica napus* (AACC, 2n=38).

"Oilseed rape" or "*Brassica* oilseed" or "oilseed crop" refers to oilseed rape *Brassica napus* cultivated as a crop.

In a further aspect, the Ogura restorer of said *Brassica* plant is present at the end of chromosome N10. In yet another aspect, said Ogura restorer is present downstream of nucleotide 19.218,577 of chromosome N10, whereas in another aspect, said Ogura restorer is characterized by the presence of markers M2, M3 and M5, and by the absence of markers M1 and M4.

In another embodiment, said Ogura restorer is characterized by the presence of a *Raphanus* chromosome fragment between position 8,330,119 and 10,655,049 of the *Raphanus* chromosome R09 or a part thereof. In yet another embodiment, the *Brassica* plant according to the invention is a *Brassica napus* WOSR plant or a *Brassica napus* SOSR plant. In a further embodiment, said the Ogura restorer of said *Brassica* plant is obtainable from reference seeds deposited at NCIMB under accession number NCIMB 43628. In another the *Brassica* plant according to the invention restores the fertility of a CMS-Ogura *Brassica napus* plant. In a further embodiment, the Ogura restorer is present in homozygous form, whereas in another embodiment the *Brassica* plant according to the invention Ogura restorer in homozygous form is an inbred plant. In yet a further embodiment, the Ogura restorer is present in heterozygous form, whereas in another embodiment the *Brassica* plant according to the invention Ogura restorer in heterozygous form is a hybrid plant, said hybrid plant optionally further containing CMS-Ogura. Also provided is a part, seed or progeny of the *Brassica* plant according to the invention. Also provided is hybrid seed comprising the Ogura restorer according to the invention.

"Upstream" of a certain position on a genome reference sequence refers to the 5' direction. With reference to the genome reference sequence, the upstream direction refers to a lower number of said position.

"Downstream" of a certain position on a genome reference sequence refers to the 3' direction. With reference to the genome reference sequence, the upstream direction refers to a higher number of said position.

Reference to chromosome N10 of *Brassica napus* is made with regard to the Darmor-bzh (version 8.1) genome sequence as described by Bayer et al., 2017, Plant Biotech J. 15, p. 1602.

Reference to the *Raphanus* chromosome R09 is made with regard to the XYB36-2 (v2.20) *Raphanus* genome (Xiaohui et al. 2015, Horticultural Plant Journal, 1(3):155-164).

"Winter oilseed rape" or "WOSR" is *Brassica* oilseed which is planted in late summer to early autumn, overwinters, and is harvested the following summer. WOSR generally requires vernalization to flower.

"Spring oilseed rape" or "SOSR" is *Brassica* oilseed which is planted in the early spring and harvested in late summer. SOSR does not require vernalization to flower.

The Ogura restorer according to the invention, or Rfo-N10, can be obtainable from or obtained from reference seeds deposited at NCIMB under accession number NCIMB 43628. Rfo-N10 can be the same as Rfo-N10 in the seeds deposited at NCIMB under accession number NCIMB 43628. The *Raphanus* fragment of Rfo-N10 can be the same as the *Raphanus* fragment present in the seeds deposited at NCIMB under accession number NCIMB 43628. The position of Rfo-N10 in the *Brassica napus* chromosome N10 can be the same as in the seeds deposited at NCIMB under accession number NCIMB 43628. Rfo-N10 can, but does not necessarily have to be derived or obtained from the seeds deposited at NCIMB under accession number NCIMB 43628. Rfo-N10 can be derived or obtained from the seeds deposited at NCIMB under accession number NCIMB 43628 through breeding.

As used herein, the term "homozygous" means that both homologous chromosomes contain the Ogura restorer according to the invention. As used herein, the term "heterozygous" means that only one chromosome of a pair of homologous chromosomes contains the Ogura restorer according to the invention.

As used herein, the term "homologous chromosomes" means chromosomes that contain information for the same biological features and contain the same genes at the same loci but possibly different alleles of those genes. Homologous chromosomes are chromosomes that pair during meiosis.

An "inbred plant" or "inbred line" is a plant or line is a pure line, or nearly homozygous line, usually developed by inbreeding.

A "hybrid plant" is a plant which is typically created in a cross between two inbred parent lines. A hybrid plant has a high level of heterozygosity. A hybrid plant may or may not show hybrid vigor (or heterosis), i.e. an increase in characteristics, such as yield, over those of its parents.

Hybrid seed is the seed resulting from a pollination of an inbred female plant with pollen from an inbred male plant. When planted, hybrid seed grows into a hybrid plant.

A hybrid plant can be produced by crossing a male sterile female inbred plant, such as a plant comprising CMS-Ogu, with a male inbred plant comprising a fertility restorer, such as an Ogura restorer, in homozygous form. The resulting hybrid plant can comprise the fertility restorer in heterozygous form.

"Male sterile" as used herein refers to a plant incapable of producing fertile, viable pollen.

A "fertility restorer" as used herein refers to a gene which upon expression in a plant comprising a male-sterility gene, is capable of preventing phenotypic expression of the male-sterility gene, restoring fertility in the plant.

In yet another embodiment, the *Brassica* plant, part seed or progeny thereof or the hybrid seed according to the invention further comprise a technically induced mutant, such as an EMS induced mutant, or a modification in the genome created with genome editing technologies, or a transgene. In another aspect, said technically induced mutant confers herbicide tolerance, such as tolerance to imidazolinone, or said transgene is a gene conferring herbicide tolerance, such as a gene which confers resistance to glufosinate or to glufosinate ammonium or a gene conferring resistance to glyphosate.

A technically induced mutant, as used herein, is a non-naturally occurring mutant created by man. A technically induced mutant can be produced through mutagenesis. "Mutagenesis" or "induced variation", as used herein, refers to the process in which plant cells (e.g., a plurality of *Brassica* seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), or a combination of two or more of these. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Mutagenesis can comprise random mutagenesis, or can comprise targeted mutagenesis. Mutagenesis can also result in epimutations that cause epigenetic silencing.

Examples of technically induced mutants in *Brassica napus* suitable to the invention mutants in the FATB gene as described in WO2009/007091 or in the FAD3 genes as described in WO2011/060946, or may be podshatter resistant mutant such as mutants described in WO2009/068313 or in WO2010/006732, or mutations conferring herbicide tolerance such as the PM1 and PM2 mutations conferring imidazolinone tolerance (Tan et al., (2005) Pest Management Science 6: 246-257 and U.S. Pat. No. 5,545,821). Podshatter resistant mutations may be obtainable from seeds having been deposited at the American Type Culture Collection (ATCC, 10801 University Boulevard, Manassas, VA 20110-2209, US) on Nov. 20, 2007, under accession number PTA-8795 or PTA-8796, or at the NCIMB Limited (Ferguson Building, Craibstone Estate, Bucksburn, Aberdeen, Scotland, AB21 9YA, UK) on Jul. 7, 2008, under accession number NCIMB 41570, NCIMB 41571, NCIMB 41572, NCIMB 41573, NCIMB 41574, or NCIMB 41575. Imidazolinone tolerant mutations may be mutations obtainable from seeds having been deposited at the American Type Culture Collection, 12301 Parklawn Drive, Rockville, Md. 20852, U.S.A., under Accession No. 40683 or 40684.

Genome editing, also called gene editing, genome engineering, as used herein, refers to the targeted modification of genomic DNA in which the DNA may be inserted, deleted, modified or replaced in the genome. Genome editing may use sequence-specific enzymes (such as endonuclease, nickases, base conversion enzymes) and/or donor nucleic acids (e.g. dsDNA, oligo's) to introduce desired changes in the DNA. Sequence-specific nucleases that can be programmed to recognize specific DNA sequences include meganucleases (MGNs), zinc-finger nucleases (ZFNs), TAL-effector nucleases (TALENs) and RNA-guided or DNA-guided nucleases such as Cas9, Cpf1, CasX, CasY, C2c1, C2c3, certain Argonaut-based systems (see e.g. Osakabe and Osakabe, Plant Cell Physiol. 2015 March; 56(3):389-400; Ma et al., Mol Plant. 2016 Jul. 6; 9(7):961-74; Bortesie et al., Plant Biotech J, 2016, 14; Murovec et al., Plant Biotechnol J. 15:917-926, 2017; Nakade et al., Bioengineered Vol 8, No. 3:265-273, 2017; Burstein et al., Nature 542, 37-241; Komor et al., Nature 533, 420-424, 2016; all incorporated herein by reference). Donor nucleic acids can be used as a template for repair of the DNA break induced by a sequence specific nuclease. Donor nucleic acids can also be used as such for genome editing without DNA break induction to introduce a desired change into the genomic DNA.

A transgene refers DNA sequences integrated into the genome through transformation.

The gene conferring herbicide resistance may be the bar or pat gene, which confer resistance to glufosinate ammonium (Liberty®, Basta® or Ignite®) [EP 0 242 236 and EP 0 242 246 incorporated by reference]; or any modified EPSPS gene, such as the 2mEPSPS gene from maize [EPO 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance.

The plants according to the invention which additionally contain a gene which confers resistance to glufosinate ammonium (Liberty®, Basta® or Ignite®) may contain a gene coding for a phosphinothricin-N-acetyltransferase (PAT) enzyme, such as a coding sequence of the bialaphos resistance gene (bar) of *Streptomyces hygroscopicus*. Such plants may, for example, comprise the elite event RF-BN1 as described in WO01/41558.

The plants according to the invention which contain a gene which confers resistance to glyphosate (RoundupReady®) may contain a glyphosate resistant EPSPS, such as a CP4 EPSPS, or an N-acetyltransferase (gat) gene. Such plants may, for example, comprise the elite event RT73 as described in WO02/36831, or elite event MON88302 as described in WO11/153186, or event DP-073496-4 as described in WO2012/071040.

Also provided herein is a method for identifying a *Brassica napus* plant comprising the Ogura restorer according to the invention, said method comprising determining the presence of a *Raphanus* marker for Rfo-N10 in the genomic DNA of said plant. In another aspect, said marker is a marker in the region comprising nucleotide 8,600,416 to 9,251,274 of *Raphanus* chromosome R09, whereas in another aspect said marker is marker M2, M3 or M5.

A "molecular marker", or a "marker", as used herein, refers to a polymorphic locus, i.e. a polymorphic nucleotide (a so-called single nucleotide polymorphism or SNP) or a polymorphic DNA sequence (which can be insertion or deletion of a specific DNA sequence at a specific locus, such as the inserted Rfo DNA sequence in the *Brassica* plant according to the invention, or polymorphic DNA sequences). A marker refers to a measurable, genetic characteristic with a fixed position in the genome, which is normally inherited in a Mendelian fashion. Thus, a molecular marker may be a short DNA sequence, such as a sequence surrounding a single base-pair change, i.e. a single nucleotide polymorphism or SNP, or a long DNA sequence, such as microsatellites or Simple Sequence Repeats (SSRs). The nature of the marker is dependent on the molecular analysis used and can be detected at the DNA, RNA or protein level. Genetic mapping can be performed using molecular markers such as, but not limited to, RFLP (restriction fragment length polymorphisms; Botstein et al. (1980), Am J Hum Genet 32:314-331; Tanksley et al. (1989), Bio/Technology 7:257-263), RAPD [random amplified polymorphic DNA; Williams et al. (1990), NAR 18:6531-6535], AFLP [Amplified Fragment Length Polymorphism; Vos et al. (1995) NAR 23:4407-4414], SSRs or microsatellites [Tautz et al. (1989), NAR 17:6463-6471]. Appropriate primers or probes are dictated by the mapping method used.

The term "AFLP®" (AFLP® is a registered trademark of KeyGene N. V., Wageningen, The Netherlands), "AFLP analysis" and "AFLP marker" is used according to standard terminology [Vos et al. (1995), NAR 23:4407-4414; EP0534858; http://www.keygene.com/keygene/techs-apps/]. Briefly, AFLP analysis is a DNA fingerprinting technique which detects multiple DNA restriction fragments by means of PCR amplification. The AFLP technology usually comprises the following steps: (i) the restriction of the DNA with two restriction enzymes, preferably a hexa-cutter and a tetra-cutter, such as EcoRI, PstI and MseI; (ii) the ligation of double-stranded adapters to the ends of the restriction fragments, such as EcoRI, PstI and MseI adaptors; (iii) the amplification of a subset of the restriction fragments using two primers complementary to the adapter and restriction site sequences, and extended at their 3' ends by one to three "selective" nucleotides, i.e., the selective amplification is achieved by the use of primers that extend into the restriction fragments, amplifying only those fragments in which the primer extensions match the nucleotides flanking the restriction sites. AFLP primers thus have a specific sequence and each AFLP primer has a specific code (the primer codes and their sequences can be found at the Keygene website: http://www.keygene.com/keygene/pdf/PRIMERCO.pdf; herein incorporated by reference); (iv) gel electrophoresis of the amplified restriction fragments on denaturing slab gels or cappilaries; (v) the visualization of the DNA fingerprints by means of autoradiography, phosphor-imaging, or other methods. Using this method, sets of restriction fragments may be visualized by PCR without knowledge of nucleotide sequence. An AFLP marker, as used herein, is a DNA fragment of a specific size, which is generated and visualized as a band on a gel by carrying out an AFLP analysis. Each AFLP marker is designated by the primer combination used to amplify it, followed by the approximate size (in base pairs) of the amplified DNA fragment. It is understood that the size of these fragments may vary slightly depending on laboratory conditions and equipment used. Every time reference is made herein to an AFLP marker by referring to a primer combination and the specific size of a fragment, it is to be understood that such size is approximate, and comprises or is intended to include the slight variations observed in different labs. Each AFLP marker represents a certain locus in the genome.

The term "SSR" refers to Simple Sequence Repeats or microsatellite [Tautz et al. (1989), NAR 17:6463-6471]. Short Simple Sequence stretches occur as highly repetitive elements in all eukaryotic genomes. Simple sequence loci usually show extensive length polymorphisms. These simple sequence length polymorphisms (SSLP) can be detected by polymerase chain reaction (PCR) analysis and be used for identity testing, population studies, linkage analysis and genome mapping.

It is understood that molecular markers can be converted into other types of molecular markers. When referring to a specific molecular marker in the present invention, it is understood that the definition encompasses other types of molecular markers used to detect the genetic variation originally identified by the specific molecular markers. For example, if an AFLP marker is converted into another molecular marker using known methods, this other marker is included in the definition. For example, AFLP markers can be converted into sequence-specific markers such as, but not limited to STS (sequenced-tagged-site) or SCAR (sequence-characterized-amplified-region) markers using standard technology as described in Meksem et al. [(2001), *Mol Gen Genomics* 265(2):207-214], Negi et al. [(2000), *TAG* 101:

146-152], Barret et al. (1989), *TAG* 97:828-833], Xu et al. [(2001), *Genome* 44(1):63-70], Dussel et al. [(2002), *TAG* 105:1190-1195]- or Guo et al. [(2003), *TAG* 103:1011-1017]. For example, Dussel et al. [(2002), *TAG* 105:1190-1195] converted AFLP markers linked to resistance into PCR-based sequence tagged site markers such as indel (insertion/deletion) markers and CAPS (cleaved amplified polymorphic sequence) markers.

Suitable molecular markers are, for example SNP markers (Single Nucleotide Polymorphisms), AFLP markers, microsatellites, minisatellites, Random Amplified Polymorphic DNA's (RAPD) markers, RFLP markers, Sequence Characterized Amplified Regions (SCAR) markers, and others, such as TRAP markers described by Hu et al. 2007, Genet Resour Crop Evol 54: 1667-1674).

Methods and assays for marker detection, or for analyzing the genomic DNA for the presence of a marker, are widely known in the art. The presence of a marker can, for example be detected in hybridization-based methods (e.g. allele-specific hybridization), using Taqman, PCR-based methods, oligonucleotide ligation based methods, or sequencing-based methods.

A useful assay for detection of SNP markers is for example KBioscience Competitive Allele-Specific PCR. For developing the KASP-assay 70 base pairs upstream and 70 basepairs downstream of the SNP are selected and two allele-specific forward primers and one allele specific reverse primer is designed. See e.g. Allen et al. 2011, Plant Biotechnology J. 9, 1086-1099, especially p1097-1098 for KASP assay method (incorporated herein by reference).

A *Raphanus* marker for Rfo-N10 can be developed using methods known in the art. New markers suitable for the invention can be developed based on the sequence of the *Raphanus* fragment in Rfo-N10 ("*Raphanus* Rfo-N10 fragment"), such as the sequence of nucleotide 8,600,416 to 9,251,274 of *Raphanus* chromosome R09. Sequences of the *Raphanus* Rfo-N10 fragment can be derived from the XYB36-2 (v2.20) *Raphanus* genome (Xiaohui et al. 2015, Horticultural Plant Journal, 1(3):155-164).

The absence of Rfo-N10 can be determined by the absence of Rfo-N10 marker.

Analysis for the presence of markers according to the invention can be performed with a first primer and a second primer, and, optionally, a probe, selected from the group consisting of a first primer consisting of a sequence of 15 to 30 nucleotides, or 15 to 25 nucleotides, or 18 to 22 nucleotides of the *Raphanus* Rfo-N10 sequences according to the invention, a second primer being complementary to a sequence of 15 to 30 nucleotides, or 15 to 25 nucleotides, or 18 to 22 nucleotides of the *Raphanus* Rfo-N10 sequences according to the invention, and wherein the distance between said first and said second primer on the *Raphanus* Rfo-N10 sequences is between 1 and 400 bases, or between 1 and 150 bases, and wherein the first primer is located, with respect to *Raphanus* Rfo-N10 sequence, upstream of said second primer, and a probe which is identical to at least 15 nucleotides, or at least 18 nucleotides, but not more than 25 nucleotides, or not more than 22 nucleotides of the sequence of the *Raphanus* Rfo-N10 sequence between said first and said second primer, provided that either the sequence of the first primer, or the sequence of the second primer, or the sequence of said probe is not present in the corresponding locus in a non-restoring *Brassica napus* plant. Said probe may be labelled, such as, for example, described in U.S. Pat. No. 5,538,848.

Analysis for the presence of markers according to the invention can be performed with a probe that hybridizes to the Rfo-N10 sequence.

Identification of PCR products specific for the Rfo-N10 can occur e.g. by size estimation after gel or capillary electrophoresis; by evaluating the presence or absence of the PCR product after gel or capillary electrophoresis; by direct sequencing of the amplified fragments; or by fluorescence-based detection methods.

Markers may be markers M2, M3 and M5, or markers linked to M2, M3 and M5.

The terms "genetically linked", "linked", "linked to" or "linkage", as used herein, refers to a measurable probability that genes or markers located on a given chromosome are being passed on together to individuals in the next generation. Thus, the term "linked" may refer to one or more genes or markers that are passed together with a gene with a probability greater than 0.5 (which is expected from independent assortment where markers/genes are located on different chromosomes). Because the proximity of two genes or markers on a chromosome is directly related to the probability that the genes or markers will be passed together to individuals in the next generation, the term genetically linked may also refer herein to one or more genes or markers that are located within about 50 centimorgan (cM) or less of one another on the same chromosome. Genetic linkage is usually expressed in terms of cM. Centimorgan is a unit of recombinant frequency for measuring genetic linkage, defined as that distance between genes or markers for which one product of meiosis in 100 is recombinant, or in other words, the centimorgan is equal to a 1% chance that a marker at one genetic locus on a chromosome will be separated from a marker at a second locus due to crossing over in a single generation. It is often used to infer distance along a chromosome. The number of base-pairs to which cM correspond varies widely across the genome (different regions of a chromosome have different propensities towards crossover) and the species (i.e. the total size of the genome). Thus, in this respect, the term linked can be a separation of about 50 cM, or less such as about 40 cM, about 30 cM, about 20 cM, about 10 cM, about 7.5 CM, about 6 cM, about 5 CM, about 4 cM, about 3 cM, about 2.5 CM, about 2 cM, or even less.

A "locus" (plural loci) as used herein is the position that a gene occupies on a chromosome. This position can be identified by the location on the genetic map of a chromosome. Included in this definition is the fragment (or segment) of genomic DNA of the chromosome on which the genes located. A QTL (quantitative trait locus), as used herein, refers to a position on the genome that corresponds to a measurable characteristic, i.e. a trait.

As used herein, a "genetic map" or "linkage map" is a table for a species or experimental population that shows the position of its genetic markers relative to each other in terms of recombination frequency. A linkage map is a map based on the frequencies of recombination between markers during crossover of homologous chromosomes.

Plants comprising Rfo-N10 can be selected using marker-assisted selection. "Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically and/or physically linked to Rfo-N10, can be used to detect and/or select plants comprising Rfo-N10. The closer the genetic linkage of the molecular marker to the locus, the less likely it is that the marker is dissociated from the locus through meiotic recombination.

In another embodiment, a method according to the invention for identifying a *Brassica napus* plant comprising the Ogura restorer is provided, said method further comprising determining the absence of a *Raphanus* marker absent in Rfo-N10 in the genomic DNA of said plant. In another aspect, said marker absent in Rfo-N10 is a marker in the region upstream of and including position 8,330,119 of *Raphanus* chromosome R09, or is a marker in the region downstream of and including position 10,655,049 excluding position 15,447,221-15,450,692, whereas in yet another aspect, said marker absent in Rfo-N10 is marker M1 or M4.

Markers that are absent in Rfo-N10 can be developed as described herein above based on the *Raphanus* sequences that are absent in Rfo-N10. Markers absent in Rfo-N10 can be markers M1 or M4, but can, for example, also be markers linked to M1 or M4 in the *Raphanus* genome.

Also provided is a method for selecting a *Brassica napus* plant comprising the Ogura restorer according to the invention said method comprising identifying the presence of a *Raphanus* marker for Rfo-N10 according to the invention, and selecting a *Brassica napus* plant comprising said *Raphanus* marker for Rfo-N10.

It is another object of the invention to provide a method for producing a *Brassica napus* plant comprising the Ogura restorer according to the invention, said method comprising crossing a first *Brassica napus* plant comprising the Ogura restorer according to the invention with a second *Brassica napus* plant; and identifying, and optionally selecting, a progeny plant comprising Rfo-N10 according to the invention. Rfo-N10 can be introduced into a *Brassica napus* plant by backcrossing. "Backcrossing" refers to a breeding method by which a (single) trait, such male sterility, can be transferred from one genetic background (a "donor") into another genetic background (i.e. the background of a "recurrent parent"), e.g. a plant not comprising Rfo-N10. An offspring of a cross (e.g. an F1 plant obtained by crossing a plant containing Rfo-N10 with a plant lacking Rfo-N10; or an F2 plant or F3 plant, etc., obtained from selfing the F1) is "backcrossed" to the parent ("recurrent parent"). After repeated backcrossing (BC1, BC2, etc.) and optionally selfings (BC1F1, BC2F1, etc.), the trait of the one genetic background is incorporated into the other genetic background.

Also provided is method for producing hybrid *Brassica napus* seed, said method comprising providing a male *Brassica napus* plant comprising the Ogura restorer according to the invention, wherein said Ogura restorer is present in homozygous form; providing a female *Brassica napus* plant comprising CMS-Ogura; crossing said female *Brassica napus* plant with said male *Brassica napus* plant; and optionally harvesting seeds. A hybrid seed produced with said method is also provided herein, as well as a hybrid *Brassica napus* plant produced from said seed.

A further embodiment provides the use of the plant according to the invention for producing hybrid seed, and the use of the plant according to the invention for breeding.

Also provided herein is a method for the protection of a group of cultivated plants comprising technically induced mutant confers herbicide tolerance, such as tolerance to imidazolinone, or a transgene conferring herbicide tolerance, such as a gene which confers resistance to glufosinate or to glufosinate ammonium or a gene conferring resistance to glyphosate, according to the invention, in a field wherein weeds are controlled by the application of a composition comprising one or more herbicidal active ingredients, such as an imidazolinone herbicide, such as imazamox, or glufosinate or glufosinate ammonium or glyphosate.

Suitable imidazolinone herbicides include, but are not limited to, Imazamox, Imazethapyr, Imazapyr, or Imazapic, or a combination thereof.

The composition may comprise additional herbicidal active ingredients having the same or a different mode of action.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the fertility restorer properties), such as seed obtained by selfing or crossing, e.g. hybrid seed (obtained by crossing two inbred parental lines), hybrid plants and plant parts derived there from are encompassed herein, unless otherwise indicated.

The plants according to the invention may further be canola quality plants.

"Canola quality" or "canola quality oil" is an oil that contains less than 2% erucic acid, and less than 30 micromoles of glucosinolates per gram of air-dried oil-free meal.

"Erucic acid" as used herein is a monounsaturated omega-9 fatty acid, denoted 22:109, or 22:1.

Seeds of the plants according to the invention are also provided.

Also provided herein is a chromosome fragment, which comprises the Rfo-N10 *Raphanus* fragment, as described throughout the specification. In one aspect the chromosome fragment is isolated from its natural environment. In another aspect it is in a plant cell, especially in a *Brassica napus* cell. Also an isolated part of the chromosome fragment comprising the the Rfo-N10 *Raphanus* fragment located on chromosome N10 of *Brassica napus* is provided herein. Such a chromosome fragment can for example be a contig or a scaffold.

Hybrid seeds of the plants according to the invention may be generated by crossing two inbred parental lines, wherein one of the inbred parental lines comprises Rfo-N10 according to the invention. The other inbred parental line may be male sterile, such as a line comprising cytoplasmic male sterility (CMS), such as Ogura (OGU) cytoplasmic male sterility. The inbred line may comprise Rfo-N10 in homozygous form. The hybrid may contain Rfo-N10 in heterozygous form. In order to produce pure hybrid seeds, the male sterile line is pollinated with pollen of the line comprising Rfo-N10. By growing parental lines in rows and only harvesting the F1 seed of the male sterile parent, pure hybrid seeds are produced.

Suitable to the invention is an isolated nucleic acid molecule comprising Rfo-N10, wherein Rfo-N10 is located on chromosome N10 of *Brassica napus*, more particularly at the end of chromosome N10, more particularly downstream of nucleotide 19.218,577 of chromosome N10.

"Isolated DNA" or an "isolated nucleic acid" as used herein refers to DNA not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

Suitable to the invention is also a kit for detecting the presence of Rfo-N10 in a biological sample. A "kit", as used herein, refers to a set of reagents for the purpose of performing the method of the invention, more particularly, the identification of Rfo-N10 in biological samples or the determination of the zygosity status of plant material comprising Rfo-N10. More particularly, a preferred embodiment of the kit of the invention comprises at least two specific primers for identification of Rfo-N10, or at least two or three specific primers for the determination of the zygosity status. Optionally, the kit can further comprise any other reagent. Alternatively, according to another embodiment of this invention, the kit can comprise at least one specific probe, which specifically hybridizes with nucleic acid of biological samples to identify the presence of Rfo-N10 therein, or at least two or three specific probes for the determination of the zygosity status. Optionally, the kit can further comprise any other reagent (such as but not limited to hybridizing buffer, label) for identification of Rfo-N10 in biological samples, using the specific probe.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

In particular, the methods and kits according to the invention are suitable to determine the presence of Rfo-N10. The presence of Rfo-N10 can be determined using at least one molecular marker, wherein said one molecular marker is linked to the presence of Rfo-N10 as defined herein.

Kits can be provided containing primers and/or probes specifically designed to detect the markers according to the invention. The components of the kits can be specifically adjusted, for purposes of quality control (e.g., purity of seed lots), detection of the presence or absence of Rfo-N10 in plant material or material comprising or derived from plant material, such as but not limited to food or feed products.

Rfo-N10 according to the invention can be used to develop molecular markers by developing primers specifically recognizing sequences in Rfo-N10.

The term "recognizing" as used herein when referring to specific primers, refers to the fact that the specific primers specifically hybridize to a specific nucleic acid sequence under the conditions set forth in the method (such as the conditions of the PCR identification protocol), whereby the specificity is determined by the presence of positive and negative controls.

Also provided is a method of producing food, feed, or an industrial product, comprising obtaining the plant according to the invention or a part thereof; and preparing the food, feed or industrial product from the plant or part thereof. In a further object, said food or feed is oil, meal, grain, starch, flour or protein; or said industrial product is biofuel, fiber, industrial chemicals, a pharmaceutical or a nutraceutical.

In some embodiments, the plant cells of the invention, i.e. a plant cell comprising Rfo-N10 as well as plant cells generated according to the methods of the invention, may be non-propagating cells.

In one aspect, plants and plant parts according to the present invention are not exclusively obtained by means of an essentially biological process.

In another aspect, plants and plant parts according to the present invention are obtained by a technical method such as a marker assisted selection method as further described herein.

The obtained plants according to the invention can be used in a conventional breeding scheme to produce more plants with the same characteristics or to introduce the characteristic of the presence of Rfo-N10 according to the invention in other varieties of the same or related plant species, or in hybrid plants. The obtained plants can further be used for creating propagating material. Plants according to the invention can further be used to produce gametes, seeds (including crushed seeds and seed cakes), seed oil, embryos, either zygotic or somatic, progeny or hybrids of plants obtained by methods of the invention. Seeds obtained from the plants according to the invention are also encompassed by the invention.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

A "biological sample" as used herein can be a plant or part of a plant such as a plant tissue or a plant cell.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a nucleic acid which is functionally or structurally defined, may comprise additional DNA regions etc.

Rfo-N10 can also be introduced into a *Brassica napus* plant using genome editing.

All patents, patent applications, and publications or public disclosures (including publications on internet) referred to or cited herein are incorporated by reference in their entirety.

The sequence listing contained in the file named "seq_listing_202770.txt", which is 9 kilobytes (size as measured in Microsoft Windows®), contains 12 sequences SEQ ID NO: 1 through SEQ ID NO: 12 is filed herewith by electronic submission and is incorporated by reference herein.

In the description and examples, reference is made to the following sequences:

SEQ ID No. 1: Marker M1
SEQ ID No. 2: Marker M2
SEQ ID No. 3: Marker M3
SEQ ID No. 4: Marker M4
SEQ ID No. 5: Marker M5
SEQ ID No. 6: Marker M6
SEQ ID No. 7: Marker M7
SEQ ID No. 8: Marker M8
SEQ ID No. 9: Marker M9
SEQ ID No. 10: Marker M10
SEQ ID No. 11: Marker M11
SEQ ID No. 12: Marker M12

Unless stated otherwise in the Examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel F A, Brent R, Kingston R E, Moore D D, Seidman J G, Smith J A and Struhl K (eds.) (2006) Current Protocols in Molecular Biology. John Wiley & Sons, New York".

Standard materials and references are described in "Croy R D D (ed.) (1993) Plant Molecular Biology LabFax, BIOS Scientific Publishers Ltd., Oxford and Blackwell Scientific Publications, Oxford" and in "Brown T A, (1998) Molecular Biology LabFax, 2nd Edition, Academic Press, San Diego". Standard materials and methods for polymerase chain reactions (PCR) can be found in "McPherson M J and Møller SG (2000) PCR (The Basics), BIOS Scientific Publishers Ltd., Oxford" and in "PCR Applications Manual, 3rd Edition (2006), Roche Diagnostics GmbH, Mannheim or www.roche-applied-science.com".

It should be understood that a number of parameters in any lab protocol such as the PCR protocols in the below Examples may need to be adjusted to specific laboratory conditions, and may be modified slightly to obtain similar results. For instance, use of a different method for preparation of DNA or the selection of other primers in a PCR method may dictate other optimal conditions for the PCR protocol. These adjustments will however be apparent to a person skilled in the art, and are furthermore detailed in current PCR application manuals.

Examples

1. Generation and Characterization of New Rfo Fertility Restorer in Oilseed Rape New oilseed rape restorer lines carrying the Rfo gene were created by several rounds of crossings and introgressions. First, a *Brassica napus* spring oilseed rape (SOSR) containing the Rfo fertility restorer was identified (Rfo CMS-BC2F1; see FIG. 1).

The restorer fragment in the SOSR BC3F2 line (see FIG. 1) was characterized using *Raphanus*-specific molecular markers (Table 1). The markers were mapped to the XYB36-2 (v2.20) *Raphanus* genome (Xiaohui et al. 2015, Horticultural Plant Journal, 1(3):155-164) and were all specific to chromosome R09. Tested markers in the region between 8,600,416 and 9,251,274 bp were positive for the *Raphanus* fragment, and tested markers in the region upstream of and including 8,330,119 bp were not present in the restorer line (not shown). All tested markers downstream of and including 10,655,049 bp, were also not present in the restorer line, with an exception of only two markers at positions 15,447,221 and 15,450,692, which were positive in the restorer line (not shown). The molecular characterization thus shows that the *Raphanus* fragment size is between 0.65 and 2.3 Mbp (i.e. the fragment between 8.3 Mbp and 10.7 Mbp at least comprising the fragment between 8.6 and 9.25 Mbp of the XYB36-2 (v2.20) *Raphanus* genome). In an ancestor line of Rfo-N10, tested markers between and including positions 8,559,668 and 10,162,058 bp of *Raphanus* chromosome R09 were positive for the *Raphanus* fragment, and tested markers in the region upstream of and including 8,330,305 bp, and downstream of and including 10,655,049 bp were not present in the restorer line (not shown). It can be assumed that the Rfo fragment is the same in Rfo-N10 and in said ancestor line, which indicates that the *Raphanus* fragment in Rfo-N10 is at least 1.56 Mbp (from 8,559,668 to 10,162,058 bp of R09) but not larger than 2.32 Mbp (between 8,330,305 and to 10,655,049 bp of R09).

TABLE 1

Mapping of the Rfo fragment in *B. napus*.

| Marker identifier | SEQ ID NO | SNP position | chromosome XYB36_22 genome (v2.20) | position XYB36_22 genome (v2.20, in bp) | *Raphanus sativus* | SOSR non-restorer | SOSR restorer |
|---|---|---|---|---|---|---|---|
| M1 | 1 | 201 | ChrR09 | 8,330,119 | TT | — | — |
| M2 | 2 | 201 | ChrR09 | 8,600,416 | TT | — | TT |
| M3 | 3 | 201 | ChrR09 | 9,251,274 | GG | — | GG |
| M4 | 4 | 201 | ChrR09 | 10,655,049 | CC | — | — |

—: no call.

From the SOSR BC2F1 Rfo line, the Rfo restorer was introgressed into a winter oilseed rape (WOSR) recurrent parent (RP2) (see, FIG. 1).

The *Raphanus* fragment carrying Rfo was genetically mapped in an F2 population derived from the Rfo-introgressed RP2. The Rfo fragment was genetically mapped after the endmost marker on chromosome A10 (N10) (M12, based on the Darmor v8.1 genome). The configuration of chromosome A10+*Raphanus* Rfo region is shown in Table 2. The data originate from a selected set of *B. napus* markers (M6 to M12, spanning the whole chromosome A10)+one *Raphanus* marker (M5) that was genetically mapped at the end of chromosome A10. The plants analyzed are positive or negative for Rfo.

TABLE 2

Configuration of chromosome A10 of *B. napus* and the *Raphanus* Rfo region in selected Rfo-positive (Rfo+) and Rfo-negative (Rfo−) plants.

| marker_identifier | SEQ ID NO | SNP position | chromosome Darmor-bzh genome (v8.1) | position Darmor-bzh genome (v8.1, in bp) | chromosome XYB36_22 genome (v2.20) | position XYB36_22 genome (v2.20, in bp) |
|---|---|---|---|---|---|---|
| M6 | 6 | 101 | A10 | 1,588,417 | | |
| M7 | 7 | 151 | A10 | 7,059,709 | | |
| M8 | 8 | 61 | A10 | 10,583,109 | | |

TABLE 2-continued

Configuration of chromosome A10 of *B. napus* and the *Raphanus* Rfo region in selected Rfo-positive (Rfo+) and Rfo-negative (Rfo−) plants.

| | | | | | | |
|---|---|---|---|---|---|---|
| M9 | 9 | 151 | A10 | 14,207,544 | | |
| M10 | 10 | 151 | A10 | 17,223,566 | | |
| M11 | 11 | 61 | A10 | 18,210,057 | | |
| M12 | 12 | 61 | A10 | 19,218,577 | | |
| M5 | 5 | 150 | | | R09 | 9,375,318 |

| marker_identifier | *Raphanus sativus* Rfo+ | SOSR RP Rfo− | BC1F1 (SOSR background) Rfo+ | BC2F1 (SOSR background) Rfo+ | WOSR RP Rfo− | BC1F1 (WOSR background) Rfo+ |
|---|---|---|---|---|---|---|
| M6 | No Call | AA | AA | AA | CC | CC |
| M7 | No Call | TT | TT | TT | CC | CC |
| M8 | No Call | GG | GG | GG | TT | TT |
| M9 | No Call | TT | TT | TT | CC | CC |
| M10 | No Call | AA | AA | AA | GG | GG |
| M11 | No Call | GG | AG | GG | AA | AA |
| M12 | No Call | CC | CC | CC | TT | TT |
| M5 | AA | No Call | AA | AA | No Call | AA |

The *Brassica napus* Rfo restorer lines were thus obtained with the short Rfo fragment as described above attached to the end of chromosome N10 of the *Brassica napus* genome. The *Brassica napus* with the improved restorer was therefore named Rfo-N10. No deletion of the *Brassica napus* genome that was associated with the presence of Rfo-N10 was observed in the selected restorer lines.

The presence of the Rfo fragment at the end of chromosome N10 in *Brassica napus* has several beneficial effects. It is easier to handle in breeding and introgression, as recombination at only one side of Rfo is needed. Moreover, presence of Rfo is not associated with a deletion in the *Brassica napus* chromosome. This does not only eliminate side effects caused by the deletion; it will also improve the recombination between the genomes of the *Brassica napus* parents, allowing for more efficient breeding.

*Brassica napus* seeds of Rfo-N10 have been deposited at the NCIMB (NCIMB Ltd, Ferguson Building, Craibstone Estate, Bucksburn, Aberdeen A B21 9YA, Scotland, UK) on 22 Jun. 2020, under accession number NCIMB 43628.

2. Size of Rfo Fragment in Rfo-N10 as Compared to Other Shortened Restorer Fragments The Rfo-N10 was compared to other previously described *Raphanus* restorer fragments of R2000 EP1493328 or WO2005/002324 and Primard-Brisset et al. (2005) Theor Appl Genet; 111(4):736-46), R40 (derived from the family improved for female fertility (Delourme et al (1991) Proc of the 8th Int Rapeseed Cong, Saskatoon, Canada: 1506-1510), and R113 (Primard-Brisset et al (2005) Theor Appl Genet 111: 736).

Markers M2 and M3 (giving calls in Rfo-N10) and markers M1 and M4 (not giving calls in Rfo-N10) were used to compare the Rfo fragment of Rfo-N10 with that of R40, R113 and R2000. All 4 markers were giving calls in R40, R113 and R2000 (Table 3). Those observations show that R40, R113 and R2000 have larger *Raphanus* introgressed fragments than Rfo-N10.

WO2017/025420 discloses a region in the *Raphanus* fragment of the restorer with improved podshattering tolerance. R2000, which is even longer than Rfo-N10, does not comprise the *Raphanus* region conferring podshatter tolerance (WO2017/025420 describes that the shortened *Raphanus* fragment of WO2005/002324 (which is R2000, see above) does not comprises genomic regions conferring podshatter tolerance). WO2009/100178 also discloses a shortened *Raphanus* fragment.

Thus, the *Raphanus* fragment in Rfo-N10 is shorter than that of R40, R113, R2000, and than the fragment of WO2017/025420, and appears to lack the *Raphanus* region conferring podshatter tolerance. Moreover, none of the previously described *Raphanus* restorer fragments are reported to reside on chromosome N10.

TABLE 3

Presence of markers in previously disclosed Rfo restorer fragments and order of markers on the physical map of *Raphanus* chromosome R09.

| Marker ID (current disclosure) | Chr (CM008007.1) | Phys. pos (genome = XYB36-2 v2.20) | *Raphanus sativus* control | R40 *B. napus* | R113 *B. napus* | R2000 *B. napus* | SOSR Rfo-N10 (BC3F1) | *B. napus* WT |
|---|---|---|---|---|---|---|---|---|
| M1 | Chr9 | 8,330,119 | TT | TT | TT | TT | — | — |
| M2 | Chr9 | 8,600,416 | TT | TT | TT | TT | TT | — |
| M3 | Chr9 | 9,251,274 | GG | GG | GG | GG | GG | — |
| M4 | Chr9 | 10,655,049 | CC | CC | CC | CC | — | — |

—: no call. Empty cell: not tested.

3. Agronomic Characteristics of *B. napus* Rfo-N10

3.1. Podshatter Tolerance of Rfo-N10 Lines Grown in the Greenhouse

WO2017/025420 discloses that some Ogura hybrids have an improved podshatter tolerance. Furthermore, WO2017/025420 discloses shortened *Raphanus* fragments that have lost the improved podshatter tolerance. As indicated above, the region conferring podshatter tolerance appears not present in *B. napus* Rfo-N10.

The pod characteristics of *B. napus* Rfo-N10 of the current invention were determined, and compared to those of R2000 (WO2005/002324) and to R40 (original Ogura restorer from INRA; R40 was derived from the family improved for female fertility (Delourme et al (1991) Proc of the 8th Int Rapeseed Cong, Saskatoon, Canada: 1506-1510).

To this end, Rfo-N10 was introgressed into a SOSR background (RP1) and a WOSR background (RP2) as shown in FIG. 1. As reference, R40 was introgressed in the same SOSR background (RP1) for the same number of generations as Rfo-N10, and R2000 was introgressed in the same WOSR background (RP2) for the same number of generations as Rfo-N10.

The podshatter resistance was determined with a random impact test (RIT). For the RIT 20 pods are used and shaken together with metal balls. In the first timepoint, after 10 seconds, the number of intact and closed pods are counted. The shaking is continued by doubling the time of shaking until less than 50% of the pods remain closed. The RIT is repeated twice.

Figure 2:
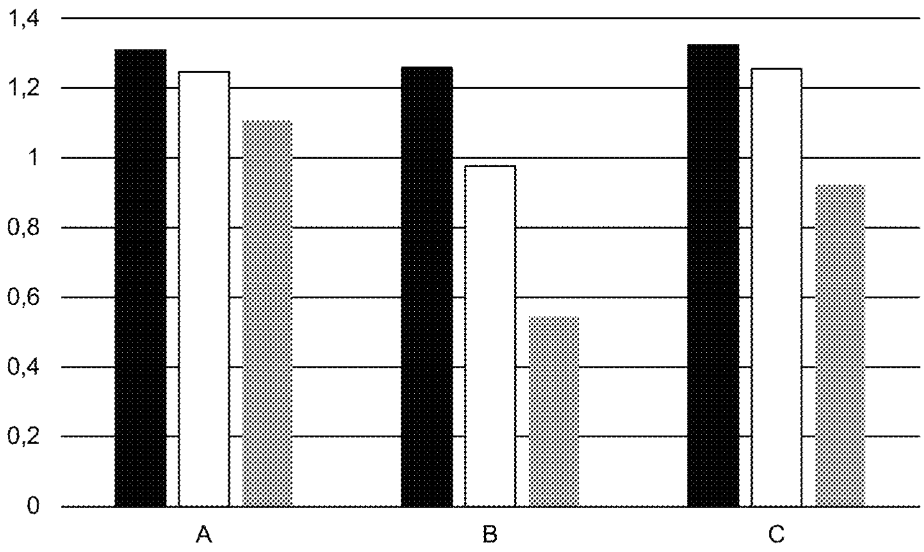
FIG. 2. RIT values of Rfo-N10 and R2000 lines. A: Rfo-N10 backcrossed in WOSR RP2 (BC3F1); B: R2000 backcrossed in WOSR RP2 (BC4F1); C: WOSR RP2. Black bars: Log 80 (average number of closed pods after additional shaking of 80 seconds); white bars: log 160 (average number of closed pods after additional shaking of 160 seconds), gray bars: average of log 320 (average number of closed pods after additional shaking of 320 seconds).
Figure 3:
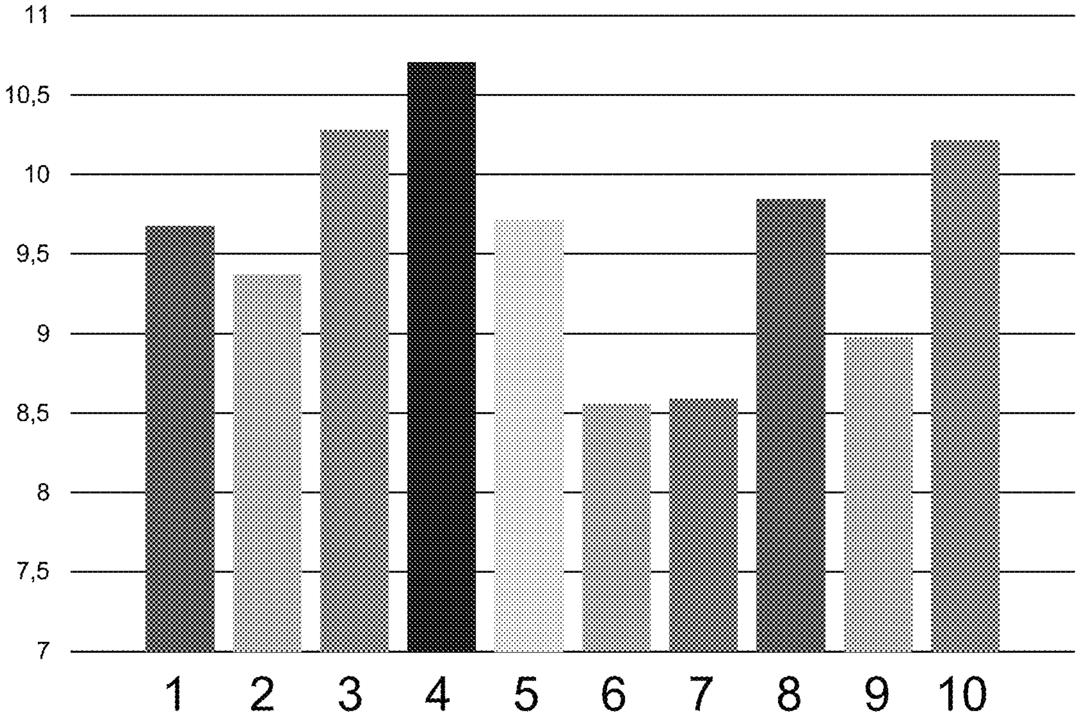
FIG. 3. Pod width values for Rfo-N10 lines as compared to R40 and R2000. Backcrosses with a SOSR Recurrent parent (RP1): 1: RP1 (SOSR); 2: BC3F1 (Hemi Rfo-N10); 3: BC3F1 (Hemi R40); 4: BC3F2 (Homo Rfo-N10); 5: BC3F2 (Hemi Rfo-N10); 6: BC3F2 (Homo R40); 7: BC3F2 (Hemi R40); Backcrosses with a WOSR RP2: 8: BC3F1 (Hemi Rfo-N10); 9: BC4F1 (Hemi R2000); 10: RP2 (WOSR).
Figure 4:
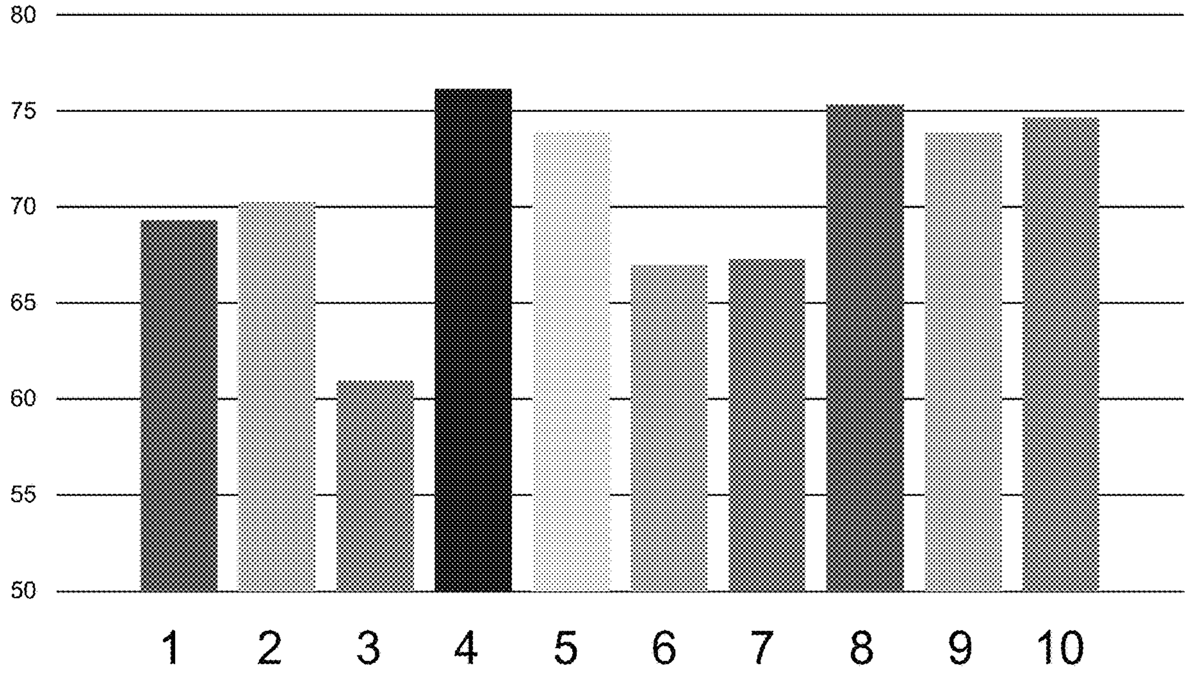
FIG. 4. Pod length values for Rfo-N10 lines as compared to R40 and R2000. Backcrosses with a SOSR Recurrent parent (RP): 1: RP1 (SOSR); 2: BC3F1 (Hemi Rfo-N10); 3: BC3F1 (Hemi R40); 4: BC3F2 (Homo Rfo-N10); 5: BC3F2 (Hemi Rfo-N10); 6: BC3F2 (Homo R40); 7: BC3F2 (Hemi R40); Backcrosses with a WOSR RP: 8: BC3F1 (Hemi Rfo-N10); 9: BC4F1 (Hemi R2000); 10: RP2 (WOSR).
Figure 5:
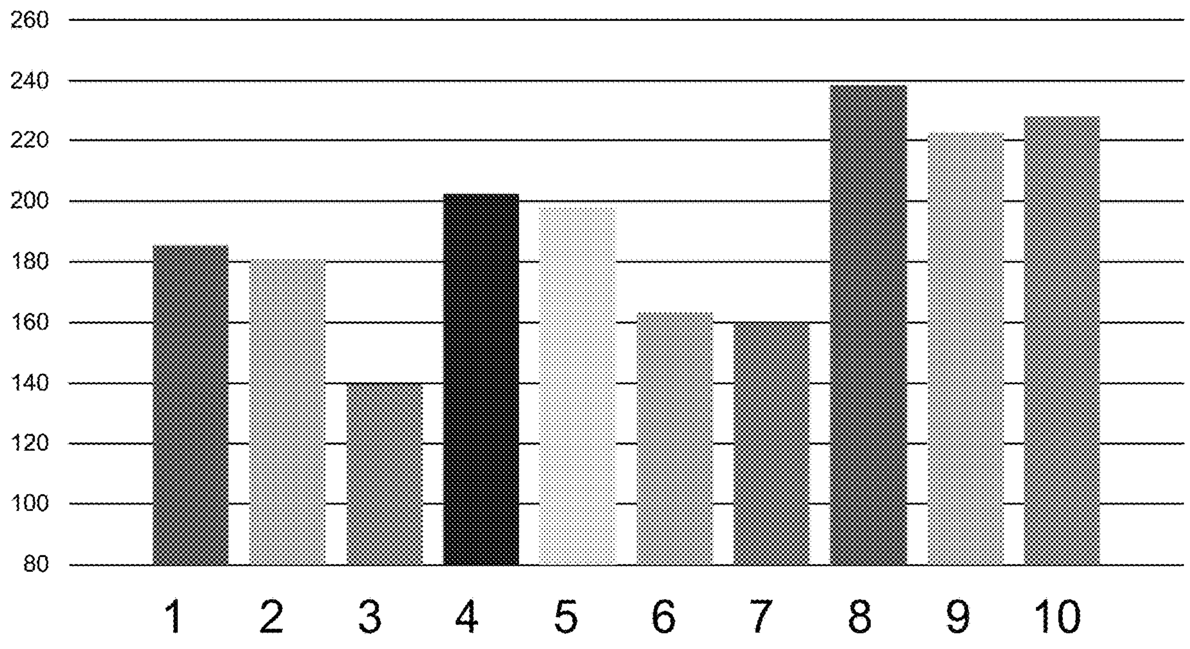
FIG. 5. Pod area values for Rfo-N10 lines as compared to R40 and R2000. Backcrosses with a SOSR Recurrent parent (RP): 1: RP1 (SOSR); 2: BC3F1 (Hemi Rfo-N10); 3: BC3F1 (Hemi R40); 4: BC3F2 (Homo Rfo-N10); 5: BC3F2 (Hemi Rfo-N10); 6: BC3F2 (Homo R40); 7: BC3F2 (Hemi R40); Backcrosses with a WOSR RP: 8: BC3F1 (Hemi Rfo-N10); 9: BC4F1 (Hemi R2000); 10: RP2 (WOSR).

FIGS. 2-5 show pod shattering values, pod width, pod length, and pod area, respectively, for the different lines gown in the greenhouse. Surprisingly, it was observed that the pod shattering values of the lines comprising Rfo-N10 were higher than those of R2000 and those of non-restoring lines (FIG. 2). This shows that, despite the absence of the region conferring podshatter tolerance as described in WO2017/025420, *B. napus* Rfo-N10 confers improved podshatter resistance. The pod width was, except for the BC3F1 generation in SOSR, consistently higher for Rfo-N10 than for R40 and R2000 and, in most cases, higher than for the recurrent parent (FIG. 3). The pod length and the pod area was, in SOSR, consistently higher for Rfo-N10 than for R40 and in most cases higher than for the recurrent parent, and in WOSR slightly higher than R2000 and similar to the recurrent parent (FIGS. 4 and 5).

3.2. Agronomic Parameters of Rfo-N10 Lines Grown in the Field

BC3F3 and FC3F4 lines of Rfo-N10 and R40, backcrossed in SOSR RP1 (see above) were grown in the field, and seed quality parameters, pod parameters, and seed parameters were tested.

Table 4 shows that the lines with Rfo-N10 have an oil content comparable to the wild-type, and canola-quality levels of glucosinolates (8.8 μmole/gram seed) and erucic acid (0% C22:1). Furthermore, Table 4 shows that the pod size parameters and seed parameters are similar or slightly better than for the wild-type, and clearly better than R40.

Table 5 shows yield and flowering time values for Rfo-N10 and R40 as compared to wild-type. It can be seen that the seed yield of Rfo-N10 is similar or slightly lower than of the wild-type, and clearly better than of R40. Moreover, Rfo-N10 is earlier in flowering than both wild-type and R40.

TABLE 4

Agronomic properties of Rfo-N10, R40 and wild-type plants. OIL_NIR = Oil content seeds at 0% moisture measured with Near Infra Red, GLUCS_NIR = Total glucosinolates content in micromole per gram seed at 0% moisure measured with Near Infra Red, TKW = average of thousand grain weight.

| Generation | Rfo-type | Rfo-state | # Plants | # Pods | # Seed lots | # Rep | Seed quality OIL_NIR |
|---|---|---|---|---|---|---|---|
| BC3F3 | Rfo-N10 | Homozygous | 3 | 50 | NA | NA | |
| BC3F3 | R40 | Homozygous | 3 | 50 | NA | NA | |
| DH (RP1) | wild type | absent | 3 | 50 | NA | NA | |
| BC3F4 | Rfo-N10 | Homozygous | NA | NA | 1 | 3 | 46.9 |
| BC3F4 | R40 | Homozygous | NA | NA | 1 | 3 | 45.9 |
| DH (RP1) | wild type | absent | NA | NA | 1 | 3 | 47.6 |

| | Seed quality | | Pod measures | | | Seed measures | | |
|---|---|---|---|---|---|---|---|---|
| Generation | GLUS_NIR | C22:1 (Wt %) | Pod length | Pod area | Pod width | Seed count | Seed weigth | TKW |
| BC3F3 | | | 81.61 | 236.3 | 9.365 | 1017 | 3.752 | 3.713 |
| BC3F3 | | | 69.54 | 192.8 | 8.089 | 870.7 | 2.723 | 3.143 |
| DH (RP1) | | | 81.47 | 227.4 | 8.723 | 969.4 | 3.515 | 3.62 |
| BC3F4 | 8.8 | 0 | | | | | | |
| BC3F4 | 8.2 | 0 | | | | | | |
| DH (RP1) | 8.1 | 0 | | | | | | |

TABLE 5

Yield and flowering properties of Rfo-N10, R40 and wild-type plants. YLD9-PC: Relative grain yield at 9% moisture percentage of checks; YLD9-BLUP: Grain yield BLUP estimate at 9% humidity; DTF: Number of days to start flowering when 10% of plants have at least one flower open; EOF: Number of days to end flowering when 90% of plants have finished flowering.

| | | | # | Yield | | Flowering | |
|---|---|---|---|---|---|---|---|
| Generation | Rfo-type | Rfo-state | Rep | YLD9-PC | YLD9-BLUP | DTF | EOF |
| DH (RP1) | wild type | absent | 3 | 100 | 2.01 | 54 | 74 |
| BC3F4 | Rfo-N10 | Homozygous | 3 | 93.03 | 1.87 | 52 | 73 |

TABLE 5-continued

Yield and flowering properties of Rfo-N10, R40 and wild-type plants. YLD9-PC: Relative grain yield at 9% moisture percentage of checks; YLD9-BLUP: Grain yield BLUP estimate at 9% humidity; DTF: Number of days to start flowering when 10% of plants have at least one flower open; EOF: Number of days to end flowering when 90% of plants have finished flowering.

| | | | # | Yield | | Flowering | |
|---|---|---|---|---|---|---|---|
| Generation | Rfo-type | Rfo-state | Rep | YLD9-PC | YLD9-BLUP | DTF | EOF |
| BC3F4 | Rfo-N10 | Homozygous | 3 | 84.58 | 1.7 | 52 | 73 |
| BC3F4 | Rfo-N10 | Homozygous | 3 | 80.1 | 1.61 | 53 | 73 |
| BC3F4 | Rfo-N10 | Homozygous | 3 | 77.61 | 1.56 | 52 | 74 |
| BC3F4 | R40 | Homozygous | 3 | 69.15 | 1.39 | 55 | 75 |
| BC3F4 | R40 | Homozygous | 3 | 63.68 | 1.28 | 55 | 76 |
| BC3F4 | R40 | Homozygous | 3 | 60.7 | 1.22 | 56 | 76 |
| | | Min | | 60.7 | 1.22 | 52 | 73 |
| | | Max | | 100 | 2.01 | 56 | 76 |
| | | Grand Mean | | 74.69 | 1.58 | 53.62 | 74.25 |
| | | Check Mean | | 100 | 2.01 | 54 | 74 |
| | | #Obs | | 32 | 32 | 32 | 32 |
| | | CV | | 10.5 | 10.5 | 0.81 | 0.58 |
| | | H2 | | 0.91 | 0.91 | 0.83 | 0.76 |
| | | LSD | | 0.12 | 0.24 | 2 | 1 |

In summary, the invention relates to the following embodiments:

1. A *Brassica napus* plant comprising an Ogura restorer on chromosome N10.

2. The *Brassica* plant of paragraph 1, wherein the Ogura restorer is present at the end of chromosome N10.

3. The *Brassica* plant according to paragraph 1 or 2, wherein said Ogura restorer is present downstream of nucleotide 19.218,577 of chromosome N10.

4. The *Brassica* plant according to any one of paragraphs 1-3, wherein said Ogura restorer is characterized by the presence of markers M2, M3 and M5, and by the absence of markers M1 and M4.

5. The *Brassica* plant according to any one of paragraphs 1-4, wherein said Ogura restorer is characterized by the presence of a *Raphanus* chromosome fragment between position 8,330,119 and 10,655,049 of the *Raphanus* chromosome or a part thereof.

6. The *Brassica* plant according to any one of paragraphs 1-5, which is a *Brassica napus* WOSR plant or a *Brassica napus* SOSR plant.

7. The *Brassica* plant according to any one of paragraphs 1-6, wherein the Ogura restorer is obtainable from reference seeds deposited at NCIMB under accession number NCIMB 43628.

8. The *Brassica* plant according to any one of paragraphs 1-7, which restores the fertility of a CMS-Ogura *Brassica napus* plant.

9. The *Brassica* plant according to any one of paragraphs 1-8, wherein the Ogura restorer is present in homozygous form.

10. The *Brassica* plant according to paragraph 9, which is an inbred plant.

11. The *Brassica* plant according to any one of paragraphs 1-8, wherein the Ogura restorer is present in heterozygous form.

12. The *Brassica* plant according to paragraph 11, which is a hybrid plant, said hybrid plant optionally further containing CMS-Ogura.

13. A part, seed or progeny of the *Brassica* plant according to any one of paragraphs 1-12.

14. Hybrid seed comprising the Ogura restorer as described in any one of paragraphs 1-7.

15. The *Brassica* plant, part seed or progeny thereof according to any one of paragraphs 1-13, or the hybrid seed according to paragraph 14, further comprising a technically induced mutant, such as an EMS induced mutant, or a modification in the genome created with genome editing technologies, or a transgene.

16. The *Brassica* plant according to paragraph 15, wherein said technically induced mutant confers herbicide tolerance, such as tolerance to imidazolinone, or wherein said transgene is a gene conferring herbicide tolerance, such as a gene which confers resistance to glufosinate or to glufosinate ammonium or a gene conferring resistance to glyphosate.

17. A method for identifying a *Brassica napus* plant comprising the Ogura restorer according to any one of paragraphs 1-16, said method comprising determining the presence of a *Raphanus* marker for Rfo-N10 in the genomic DNA of said plant.

18. The method according to paragraph 17, wherein said marker is a marker in the region comprising nucleotide 8,600,416 to 9,251,274 of *Raphanus* chromosome R09.

19. The method according to paragraph 17 or 18, wherein said marker is marker M2, M3 or M5.

20. The method according to any one of paragraphs 17-19, further comprising determining the absence of a *Raphanus* marker absent in Rfo-N10 in the genomic DNA of said plant.

21. The method according to paragraph 20, wherein said marker absent in Rfo-N10 is a marker in the region upstream of and including position 8,330,119 of *Raphanus* chromosome R09, or is a marker in the region downstream of and including position 10,655,049 excluding position 15,447,221-15,450,692.

22. The method according to paragraph 20 or 21, wherein said marker absent in Rfo-N10 is marker M1 or M4.

23. A method for selecting a *Brassica napus* plant comprising the Ogura restorer according to any one of paragraphs 1-16, said method comprising identifying the presence of a *Raphanus* marker for Rfo-N10 as described in any one of paragraphs 17-22, and selecting a *Brassica napus* plant comprising said *Raphanus* marker for Rfo-N10.

24. A method for producing a *Brassica napus* plant comprising the Ogura restorer according to any one of paragraphs 1-10, said method comprising:

a. crossing a first *Brassica* plant according to any one of paragraphs 1-16 with a second *Brassica napus* plant b. identifying, and optionally selecting, a progeny plant comprising Rfo-N10 as described in any one of paragraphs 17-23.

25. A method for producing hybrid *Brassica napus* seed, said method comprising:

a. providing a male *Brassica napus* plant comprising the Ogura restorer according to any one of paragraphs 1-16, wherein said Ogura restorer is present in homozygous form;

b. providing a female *Brassica napus* plant comprising CMS-Ogura;

c. crossing said female *Brassica napus* plant with said male *Brassica napus* plant; and optionally d. harvesting seeds.

26. Hybrid *Brassica napus* seed produced with the method according to paragraph 25.

27. A hybrid *Brassica napus* plant produced from the seed according to paragraph 26.

28. Use of the plant according to any one of paragraphs 1-16 for producing hybrid seed.

29. Use of the plant according to any one of paragraphs 1-16 for breeding.

30. A method for the protection of a group of cultivated plants according to paragraph 16 in a field wherein weeds are controlled by the application of a composition comprising one or more herbicidal active ingredients.

31. The method according to paragraph 30, wherein the plants comprise a technically induced mutant which confers tolerance to imidazolinone and wherein the herbicide is an imidazolinone, such as imazamox; or wherein the plants comprise a gene which confers resistance to glufosinate or to glufosinate ammonium and where the herbicide is glufosinate or glufosinate ammonium, or wherein the plants comprise a gene conferring resistance to glyphosate, and the herbicide is glyphosate.

The invention claimed is:

1. A *Brassica napus* plant comprising an Ogura restorer on chromosome N10 (Rfo-N10), wherein said Ogura restorer comprises markers M2, M3 and M5, and does not comprise markers M1 and M4.

2. The *Brassica napus* plant according to claim 1, wherein said Rfo-N10 restorer comprises a fragment of the *Raphanus sativus* chromosome R09.

3. The *Brassica napus* plant according to claim 1, which is a *Brassica napus* WOSR plant or a *Brassica napus* SOSR plant.

4. The *Brassica napus* plant according to claim 1, wherein the Rfo-N10 restorer is obtainable from reference seeds deposited at NCIMB under accession number NCIMB 43628.

5. The *Brassica napus* plant according to claim 1, wherein the *Brassica napus* plant is fertile and comprises a CMS-Ogura locus.

6. The *Brassica napus* plant according to claim 1, wherein the Rfo-N10 restorer is present in homozygous form.

7. The *Brassica napus* plant according to claim 6, which is an inbred plant.

8. The *Brassica napus* plant according to claim 1, wherein the Rfo-N10 restorer is present in heterozygous form.

9. The *Brassica napus* plant according to claim 8, which is a hybrid plant, said hybrid plant optionally further containing CMS-Ogura.

10. A part, seed or progeny of the *Brassica napus* plant according to claim 1, wherein the part, seed, or progeny of the *Brassica napus* plant comprise said Rfo-N10 restorer.

11. F1 hybrid seed comprising the Rfo-N10 restorer as described in claim 1.

12. The *Brassica napus* plant, part seed or progeny thereof according to claim 1, further comprising a mutation or a transgene, wherein the part, seed, or progeny of the *Brassica napus* plant comprise said Rfo-N10 restorer.

13. The *Brassica napus* plant according to claim 12, wherein said mutation confers herbicide tolerance or wherein said transgene is a gene conferring herbicide tolerance.

14. A method for identifying a *Brassica napus* plant comprising the Rfo-N10 restorer according to claim 1, said method comprising determining the presence of the M2, M3, and M5 markers and the absence of the M1 and M4 markers.

15. A method for selecting a *Brassica napus* plant comprising an Ogura restorer, said method comprising identifying the presence of a *Raphanus* marker for Rfo-N10 as described in claim 14, and selecting a *Brassica napus* plant comprising said *Raphanus* marker for Rfo-N10.

16. A method for producing a *Brassica napus* plant comprising an Ogura restorer, said method comprising:

a. crossing a first *Brassica* plant according to claim 1 with a second *Brassica napus* plant; and b. identifying, and optionally selecting, a progeny plant comprising Rfo-N10.

17. A method for producing hybrid *Brassica napus* seed, said method comprising:

a. providing a male *Brassica napus* plant comprising the Rfo-N10 restorer according to claim 1, wherein said Rfo-N10 restorer is present in homozygous form;

b. providing a female *Brassica napus* plant comprising CMS-Ogura;

c. crossing said female *Brassica napus* plant with said male *Brassica napus* plant;

and optionally d. harvesting seeds.

18. F1 hybrid *Brassica napus* seed produced with the method according to claim 17.

19. A F1 hybrid *Brassica napus* plant produced from the seed according to claim 18.

20. A method for the protection of a group of cultivated *Brassica napus* plants according to claim 13 in a field, said method comprising controlling weeds by applying a composition comprising one or more herbicidal active ingredients.

21. The method according to claim 20, wherein the plants comprise a mutation or transgene which confers tolerance to imidazolinone and wherein the herbicide is an imidazolinone; or wherein the plants comprise a mutation or transgene which confers resistance to glufosinate or to glufosinate ammonium and where the herbicide is glufosinate or glufosinate ammonium, or wherein the plants comprise a mutation or transgene conferring resistance to glyphosate, and the herbicide is glyphosate.

* * * * *

SEQUENCE LISTING

```
<160> NUMBER OF SEQ ID NOS: 12

<210> SEQ ID NO 1
<211> LENGTH: 401
<212> TYPE: DNA
<213> ORGANISM: Raphanus sativus
<220> FEATURE:
<223> OTHER INFORMATION: Marker M1
<220> FEATURE:
<221> NAME/KEY: misc_feature
<222> LOCATION: (201)..(201)
<223> OTHER INFORMATION: w means a or t

<400> SEQUENCE: 1

tatcccttct ctccgagcac atctaagctc aataaccacc tcattgccaa acaaaccgat     60

ccttagatta tcagttaaac cagcgtaacc ggtatcagct ggttcatcct ctcctacatt    120

cacatcactc tccttcctct tggtgttcaa acaattagcc gatgctctct catcttcatc    180

ttccgatttc ttccttttcg waggcattcg catctctgta tcggtatatt ctctgcaaga    240

ttccagttct tgaacccgtc tttgcagttt ttgaagataa tcaatcgtat catcaagaat    300

cgacacttta tcgatctgat aaacaacaac agataagatt acctccttca aaacatagta    360

tttcataaca tgcacataca aaacgttttc gagtctatgt c                        401


<210> SEQ ID NO 2
<211> LENGTH: 401
<212> TYPE: DNA
<213> ORGANISM: Raphanus sativus
<220> FEATURE:
<223> OTHER INFORMATION: Marker M2
<220> FEATURE:
<221> NAME/KEY: misc_feature
<222> LOCATION: (201)..(201)
<223> OTHER INFORMATION: y means t or c

<400> SEQUENCE: 2

tttttgtgta ttaaacttcc tgcattgtac atcttatata aatatttaag aacaataacg     60

ataaaatatt ataattccct tatttcccaa atatcctccc aataatctag aagctctagt    120

ctctttcacc gactccactg aatttttcaa aagagcaaaa gaaatcttta agaaatataa    180

aaaatccccg aaaaatgtct yctcccttcc taatcacatg gaccttatca acgcattatc    240

agcttacgtc ctctccgttc cgtgcagctg tattgcactt tctccacaag cgaaaacgac    300

ttcggattta cacatcacag tccttttctc tcaccaaacc ctcaccttct agaatctctt    360
```

atctcatttg cttgatatgc aagcaatata gtaaatccta a 401

<210> SEQ ID NO 3
<211> LENGTH: 401
<212> TYPE: DNA
<213> ORGANISM: Raphanus sativus
<220> FEATURE:
<223> OTHER INFORMATION: Marker M3
<220> FEATURE:
<221> NAME/KEY: misc_feature
<222> LOCATION: (201)..(201)
<223> OTHER INFORMATION: s means g or c

<400> SEQUENCE: 3
ctaatttttt ctttctcaaa ataaagttgt ttttgcttag atgacaaaaa acctgtgaat 60
gaacagattt attttcacgg taacagaaaa aagagtgcaa ataataactc aaactttagt 120
ttccttttct gaatagatga tacaagtttt cttcttcctc tttcactagc ctgtaaccac 180
tttctatttt taatttacat scatcagcta ccaaacacaa tactactaac aaaaaagtat 240
taacaaagaa aataaccttt catgttaccc tgtcaagcga gaggaaaaag aactatgtcc 300
taagatgatt gagcaagaag ttcagaaacg tcttcactag attccgacca aagcttttga 360
ctaaagtccg tttgaagctc atcaggtaca aactgggtac g 401

<210> SEQ ID NO 4
<211> LENGTH: 401
<212> TYPE: DNA
<213> ORGANISM: Raphanus sativus
<220> FEATURE:
<223> OTHER INFORMATION: Marker M4
<220> FEATURE:
<221> NAME/KEY: misc_feature
<222> LOCATION: (201)..(201)
<223> OTHER INFORMATION: r means g or a

<400> SEQUENCE: 4
aatagagatg gaaagaagac aatcatcagc taaccaaaac attcaagatc atcctccgta 60
cacttactcc caaaccgccg acaaagagaa acccaccacc aaaagaaacg tgtcggatcc 120
ggatccgaat cctatctcta tagctccagc tccaaggtca cactctcggg ctcaaacaac 180
ttctccgaca aggaacgtga ratatagaga atgccaaagg aaccacgcgg cgagctccgg 240
cggacacgtg gtcgacggtt gcggcgagtt tatgtcgtca ggcgaagaag gcacggcgga 300
gtcgcttctc tgcgccgcat gcgattgtca ccggagtttc cacagaaaag aaatcgacgg 360
catgttcgtt gtccaattca atagctttgg tcattcacag a 401

<210> SEQ ID NO 5
<211> LENGTH: 300
<212> TYPE: DNA
<213> ORGANISM: Raphanus sativus
<220> FEATURE:
<223> OTHER INFORMATION: Marker M5
<220> FEATURE:
<221> NAME/KEY: misc_feature
<222> LOCATION: (150)..(150)
<223> OTHER INFORMATION: y means t or c

<400> SEQUENCE: 5
ttcggaatct tcgatggaat actagttctg cttttaaaaa taccaaaaca aaacaaacat 60
aagaatctaa aaaaatatgt attcatattg ttctgttaaa gtgtgctagt agagggtact 120
tacttgtctt tgggcacggt tttcaccaty ttgctgattt ctcgagcttc tcagggacca 180
agtgtggttc aggttcttcc gttatttcaa gaggcttcac ggtttcaggg aaaagagtca 240
actcgactgc actgcatatg gagccatcag tttctgttcc catcgaaaga cagctatcag 300

<210> SEQ ID NO 6
<211> LENGTH: 201
<212> TYPE: DNA
<213> ORGANISM: Brassica napus
<220> FEATURE:
<223> OTHER INFORMATION: Marker M6
<220> FEATURE:
<221> NAME/KEY: misc_feature
<222> LOCATION: (34)..(34)
<223> OTHER INFORMATION: m means a or c
<220> FEATURE:
<221> NAME/KEY: misc_feature
<222> LOCATION: (101)..(101)
<223> OTHER INFORMATION: m means a or c
<220> FEATURE:
<221> NAME/KEY: misc_feature
<222> LOCATION: (108)..(108)
<223> OTHER INFORMATION: r means g or a
<220> FEATURE:
<221> NAME/KEY: misc_feature
<222> LOCATION: (113)..(113)
<223> OTHER INFORMATION: m means a or c
<220> FEATURE:
<221> NAME/KEY: misc_feature
<222> LOCATION: (165)..(165)
<223> OTHER INFORMATION: k means g or t
<220> FEATURE:
<221> NAME/KEY: misc_feature
<222> LOCATION: (177)..(177)
<223> OTHER INFORMATION: m means a or c
<220> FEATURE:
<221> NAME/KEY: misc_feature
<222> LOCATION: (182)..(182)
<223> OTHER INFORMATION: y means t or c

<400> SEQUENCE: 6
taggtacaat gctcatcttc tcttctcctt ccamggctct attgtatcca tacaaaagac 60
atatcaacag tgaatgaatc catggaactt ctcaatttga mgcaacgrat cgmaattcaa 120
tttaaaacag aaacgattgc atacttcaat gctccaaaat agagkgatta tccccamacg 180
aygaagaaca taaaaaaaaa a 201

<210> SEQ ID NO 7
<211> LENGTH: 301
<212> TYPE: DNA
<213> ORGANISM: Brassica napus
<220> FEATURE:
<223> OTHER INFORMATION: Marker M7
<220> FEATURE:
<221> NAME/KEY: misc_feature
<222> LOCATION: (31)..(31)
<223> OTHER INFORMATION: y means t or c
<220> FEATURE:
<221> NAME/KEY: misc_feature
<222> LOCATION: (34)..(34)
<223> OTHER INFORMATION: y means t or c
<220> FEATURE:
<221> NAME/KEY: misc_feature
<222> LOCATION: (46)..(46)
<223> OTHER INFORMATION: y means t or c
<220> FEATURE:
<221> NAME/KEY: misc_feature
<222> LOCATION: (151)..(151)
<223> OTHER INFORMATION: y means t or c
<220> FEATURE:
<221> NAME/KEY: misc_feature
<222> LOCATION: (161)..(161)
<223> OTHER INFORMATION: r means g or a
<220> FEATURE:
<221> NAME/KEY: misc_feature
<222> LOCATION: (297)..(297)
<223> OTHER INFORMATION: m means a or c

<400> SEQUENCE: 7
tggcatccat gaaggatata agttgatggt yggycattgc ttcgayaagc ctatcaatat 60
gtgggagtgg aaaacagcat ttcttacatg ccttgttgag ggctatgtag tcgatgcaaa 120
ctctccactg cccgtttatt tttataacta yggggttggc ragtcagtcg ggtatttta 180 cctcgcgaat attgatccaa ccttcagtag tatatatact tcgccattta ctttcgtggt 240
gctctctggg cctagcttgc aacgtttatg atttataggt ttgaacgtgg gatcggmatt 300
t 301

<210> SEQ ID NO 8
<211> LENGTH: 121
<212> TYPE: DNA
<213> ORGANISM: Brassica napus
<220> FEATURE:
<223> OTHER INFORMATION: Marker M8
<220> FEATURE:
<221> NAME/KEY: misc_feature
<222> LOCATION: (34)..(34)
<223> OTHER INFORMATION: m means a or c
<220> FEATURE:
<221> NAME/KEY: misc_feature
<222> LOCATION: (40)..(40)
<223> OTHER INFORMATION: m means a or c
<220> FEATURE:
<221> NAME/KEY: misc_feature
<222> LOCATION: (44)..(44)
<223> OTHER INFORMATION: r means g or a
<220> FEATURE:
<221> NAME/KEY: misc_feature
<222> LOCATION: (61)..(61)
<223> OTHER INFORMATION: k means g or t

<400> SEQUENCE: 8
ataacaacaa ttcactttaa tcgatagaca ccgmaaaagm accracggaa aacatatagt 60
kcatctattt agacgcatta ttatagaagc tgatgtcatt cgattacgtt gtgcagtcca 120
g 121

<210> SEQ ID NO 9
<211> LENGTH: 301
<212> TYPE: DNA
<213> ORGANISM: Brassica napus
<220> FEATURE:
<223> OTHER INFORMATION: Marker M9
<220> FEATURE:
<221> NAME/KEY: misc_feature
<222> LOCATION: (93)..(93)
<223> OTHER INFORMATION: w means a or t
<220> FEATURE:
<221> NAME/KEY: misc_feature
<222> LOCATION: (104)..(104)
<223> OTHER INFORMATION: k means g or t
<220> FEATURE:
<221> NAME/KEY: misc_feature
<222> LOCATION: (151)..(151)
<223> OTHER INFORMATION: y means t or c
<220> FEATURE:
<221> NAME/KEY: misc_feature
<222> LOCATION: (223)..(223)
<223> OTHER INFORMATION: w means a or t
<220> FEATURE:
<221> NAME/KEY: misc_feature
<222> LOCATION: (228)..(228)
<223> OTHER INFORMATION: r means g or a

<400> SEQUENCE: 9

```
tctaaaggaa gcaagattct tcagacataa gtgattgtgg atgctctgta gctgaagatg     60

cagcctgatc aacgcaaaaa ggtcccaact ttwctctctc ttckttctca agtttacata    120

acactataga tttgagatct gaataggatc ygtaacactc ccttatcatg gttcttgcag    180

tcatcagtgg aactagattt cttcacggag tacggtgaag gcwccagrta cagaatcgag    240

gaagtcatcg gcaaaggaag ctacggagtc gtctgctcgg cctacgacac gcacacggga    300

g                                                                    301


<210> SEQ ID NO 10
<211> LENGTH: 301
<212> TYPE: DNA
<213> ORGANISM: Brassica napus
<220> FEATURE:
<223> OTHER INFORMATION: Marker M10
<220> FEATURE:
<221> NAME/KEY: misc_feature
<222> LOCATION: (1)..(10)
<223> OTHER INFORMATION: n means a or g or c or t
<220> FEATURE:
<221> NAME/KEY: misc_feature
<222> LOCATION: (59)..(59)
<223> OTHER INFORMATION: r means g or a
<220> FEATURE:
<221> NAME/KEY: misc_feature
<222> LOCATION: (92)..(92)
<223> OTHER INFORMATION: y means t or c
<220> FEATURE:
<221> NAME/KEY: misc_feature
<222> LOCATION: (151)..(151)
<223> OTHER INFORMATION: r means g or a
<220> FEATURE:
<221> NAME/KEY: misc_feature
<222> LOCATION: (218)..(218)
<223> OTHER INFORMATION: y means t or c
<220> FEATURE:
<221> NAME/KEY: misc_feature
<222> LOCATION: (301)..(301)
<223> OTHER INFORMATION: y means t or c

<400> SEQUENCE: 10

nnnnnnnnnn ccctgcggct tttggtaaca acagcagcat tggtgcaagt gttcatcarc     60

agcaaatccc aaacttggct aataatccat tygctagtaa tccaggagga ggattttata    120

atcatccagt gtttcctttt ggtagcaaca rcattggtgc aagtgcttat caaccaaaca    180

tggcgaacaa tccatttgct gcttatggga acaacagygc tcctcattat cagcaagaac    240

aagtcccaac catggctaac aatccatttg ctcgtccagg aggagcaaat ccgtttcagt    300

y                                                                    301


<210> SEQ ID NO 11
<211> LENGTH: 121
<212> TYPE: DNA
<213> ORGANISM: Brassica napus
<220> FEATURE:
<223> OTHER INFORMATION: Marker M11
<220> FEATURE:
<221> NAME/KEY: misc_feature
<222> LOCATION: (61)..(61)
<223> OTHER INFORMATION: r means g or a

<400> SEQUENCE: 11

agttcatatt aaagttgtaa aaccggacta agggaggata tatatggagc ttacgagtac     60

racagagtct ctagctgcga tggctaagat atcagcacaa gacacaaccc cgggacatgc    120

t                                                                    121
```

-continued

```
<210> SEQ ID NO 12
<211> LENGTH: 121
<212> TYPE: DNA
<213> ORGANISM: Brassica napus
<220> FEATURE:
<223> OTHER INFORMATION: Marker M12
<220> FEATURE:
<221> NAME/KEY: misc_feature
<222> LOCATION: (61)..(61)
<223> OTHER INFORMATION: y means t or c
<220> FEATURE:
<221> NAME/KEY: misc_feature
<222> LOCATION: (107)..(107)
<223> OTHER INFORMATION: r means g or a
<220> FEATURE:
<221> NAME/KEY: misc_feature
<222> LOCATION: (113)..(113)
<223> OTHER INFORMATION: w means a or t
<220> FEATURE:
<221> NAME/KEY: misc_feature
<222> LOCATION: (117)..(117)
<223> OTHER INFORMATION: w means a or t

<400> SEQUENCE: 12

ctatctttca ggtaaattct tatctgtttg aattttcttg atgcacatct attcactctt     60

yatgtgtaaa atttccactt gttgagccat gttgttcttc aattacrtag gcwtctwata    120

a                                                                    121
```